US008879686B2

(12) United States Patent
Okada et al.

(10) Patent No.: US 8,879,686 B2
(45) Date of Patent: Nov. 4, 2014

(54) RADIOGRAPHIC IMAGE DETECTOR, RADIOGRAPHIC IMAGING APPARATUS, RADIOGRAPHIC IMAGING SYSTEM

(71) Applicant: FUJIFILM Corporation, Tokyo (JP)

(72) Inventors: Yoshihiro Okada, Ashigarakami-gun (JP); Naoto Iwakiri, Ashigarakami-gun (JP); Tomoki Inoue, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 49 days.

(21) Appl. No.: 13/722,510

(22) Filed: Dec. 20, 2012

(65) Prior Publication Data
US 2013/0163716 A1    Jun. 27, 2013

(30) Foreign Application Priority Data

Dec. 22, 2011  (JP) .................................. 2011-282355
Dec. 6, 2012   (JP) .................................. 2012-267524

(51) Int. Cl.
| | | |
|---|---|---|
| G01N 23/04 | (2006.01) | |
| H04N 5/32 | (2006.01) | |
| G01T 1/16 | (2006.01) | |
| H04N 5/347 | (2011.01) | |

(52) U.S. Cl.
CPC .. *H04N 5/32* (2013.01); *G01T 1/16* (2013.01); *G01N 23/046* (2013.01); *H04N 5/347* (2013.01)
USPC .............................................. 378/19; 378/62

(58) Field of Classification Search
CPC ............... G01N 23/046; A61B 6/0306; A61B 6/40085; G01T 1/2985
USPC ......................................... 378/4, 19, 98.8, 62
See application file for complete search history.

(56) References Cited

U.S. PATENT DOCUMENTS

| | | | | |
|---|---|---|---|---|
| 7,336,305 B2 * | 2/2008 | Suzuki | ........................... | 348/249 |
| 7,598,478 B2 * | 10/2009 | Morimoto et al. | .......... | 250/208.1 |
| 2001/0024237 A1 * | 9/2001 | Osada et al. | ................... | 348/273 |

FOREIGN PATENT DOCUMENTS

| | | |
|---|---|---|
| JP | 2003-23555 A | 1/2003 |
| JP | 2003-255049 A | 9/2003 |
| JP | 2004-46143 A | 2/2004 |

OTHER PUBLICATIONS

Japanese Office Action, dated Nov. 12, 2013, for Japanese Application No. 2012-267524 with an English translation.
Japanese Notice of Allowance (including full English language translation thereof), mailed Feb. 4, 2014, for corresponding Japanese Patent Application No. 2012-267524.
Japanese Office Action (including full English language translation thereof), mailed Nov. 12, 2013, for corresponding Japanese Patent Application No. 2012-267524.

* cited by examiner

*Primary Examiner* — Irakli Kiknadze
(74) *Attorney, Agent, or Firm* — Birch, Stewart, Kolasch & Birch, LLP

(57) ABSTRACT

The present invention provides a radiographic image detector that may maintain even resolution in 6 directions before and after 3-pixel binning process or 4-pixel binning process. A radiation detector is disposed with plural pixels that have hexagonal shaped pixel regions, arrayed in a honeycomb pattern. Scan lines connected to TFT switches in each of the pixels are disposed one for each of the pixel rows. Grouped scan lines are also disposed one for each of the pixel rows for reading and combining 3 pixels or 4 pixels worth of charges at the same timing for plural pixel groups, each configured from 3 pixels or 4 pixels in a radiation detection element. ON signals are simultaneously sent by the grouped scanned lines to the TFT switches to perform 3-pixel binning or 4-pixel binning.

22 Claims, 17 Drawing Sheets

RADIOGRAPHIC IMAGE DETECTOR, RADIOGRAPHIC IMAGING APPARATUS, RADIOGRAPHIC IMAGING SYSTEM

CROSS-REFERENCE TO RELATED APPLICATION

This application claims priority under 35 USC 119 from Japanese Patent Application No. 2011-282355, filed on Dec. 22, 2011, and Japanese Patent Application No. 2012-267524, filed on Dec. 6, 2012 the disclosure of which is incorporated by reference herein.

BACKGROUND OF THE INVENTION

1. Field of the Invention

The present invention relates to a radiographic image detector, a radiographic imaging apparatus and a radiographic imaging system. The present invention particularly relates to a radiographic image detector, radiographic imaging apparatus and a radiographic imaging system for direct conversion of radiation into charges.

2. Description of the Related Art

Recently, radiographic image detection apparatuses that have being put into practice employ radiation detectors such as Flat Panel Detectors (FPDs) that have a X-ray-sensitive layer disposed above a Thin Film Transistor (TFT) active matrix substrate, and are capable of directly converting X-ray data into digital data. Such FPDs have the advantage of enabling more immediate image and video image confirmation than for example conventional film screens, and their use is rapidly widening. Various types of radiation detectors are proposed, for example, there are direct-conversion-type in which radiation is directly converted into charges in a semiconductor layer and the charges accumulated, and indirect-conversion-type in which radiation is first converted into light by a scintillator, such as CsI: Tl or GOS ($Gd_2O_2S$:Tb), and then the converted light is converted into charges in a semiconductor layer and the charges accumulated.

In radiation detectors, for example, plural scan lines and plural signal lines are disposed intersecting with each other, and pixels are disposed in a matrix pattern corresponding to each of the intersections between the scan lines and the signal lines. The plural scan lines and the plural signal lines are connected to an external circuit, such as, for example an amplifier Integrated Circuit (IC) or a gate IC.

Reducing the size of the pixels in radiation detectors is an effective way to increase the resolution of FPDs. Particularly in direct-conversion-type radiation detectors employing for example Se, various radiation detectors are proposed for high definition enhanced image quality, that contribute to increasing the resolution whilst leaving the pixel size virtually unchanged. For example, products with small pixel size are proposed for FPDs for mammography where there is an emphasis on resolution.

However, simply reducing the pixel size may lead to a drop in sensitivity due to the proportional relationship to surface area in a radiation detection device. Accordingly, the use of hexagonal shaped pixels in radiation detection apparatuses in order to achieve an increase in both resolution and sensitivity is proposed (see for example Japanese Patent Application Laid-Open (JP-A) No. 2003-255049). Further, with square shaped pixels, the resolution in diagonal directions is lower than in the horizontal and vertical directions. However, employing hexagonal shaped pixels may secure high resolution in each of the horizontal, vertical and diagonal directions.

When the use of the hexagonal shaped pixels described above in still imaging and video imaging (fluoroscopic imaging) is considered, methods of reading charges from plural pixels at the same time and summing the obtained values (binning) are being considered, in particular in order to maintain a high frame rate such as in video. Performing such pixel summing within a sensor is also being considered.

However, in pixel summing of plural hexagonal shaped pixels, unevenness in pixel positions (the positions of the center of gravity when plural pixels are treated as one pixel cluster) may occur before and after summing, depending on the summing method. Accordingly, even resolution in each of the horizontal, vertical and diagonal directions that has been secured in before summing may not be maintained in after summing.

SUMMARY OF THE INVENTION

The present invention provides a radiographic image detector, a radiographic imaging apparatus and a radiographic imaging system that may maintain even resolution before and after combining the charges of plural pixels in each of the horizontal, vertical and diagonal directions.

A first aspect of the present invention is a radiographic image detector including: a detection section including a plurality of pixels having hexagonal shaped pixel regions arrayed in a honeycomb pattern, each pixel including a sensor portion that generates charges according to irradiated radiation, a first switching element that reads out the generated charges, and a second switching element that reads out the generated charges; a plurality of first scan lines, disposed one for each of a plurality of pixel rows configured by a plurality of the pixels adjacent to each other along a row direction, that are connected to a control terminal of the first switching element in each of the pixels of the corresponding pixel row; and a plurality of second scan lines, disposed one for each of a plurality of pixel groups each configured by a combination of a specific number of mutually adjacent pixels out of the plurality of pixels, that are connected to a control terminal of the second switching element in each of the pixels in the respective pixel group so as to combine and read generated charges by pixel group unit, wherein the specific number of pixels are combined such that, when a plurality of hexagonal shaped regions are placed adjacent to each other, the plurality of hexagonal shaped regions are arrayed in a honeycomb pattern, wherein each of hexagonal shaped regions are formed by including one out of a plurality of centers of gravity of the plurality of pixel groups at the inside and line segments connecting together 6 individual centers of gravity present at the periphery of the one center of gravity.

A second aspect of the present invention is a radiographic image detector including: a detection section including a plurality of pixels having hexagonal shaped pixel regions arrayed in a honeycomb pattern, each pixel including, a sensor portion that generates charges according to irradiated radiation, a first switching element that reads out the generated charges, and a second switching element that reads out the generated charges; a plurality of first scan lines, disposed one for each of a plurality of pixel rows configured by a plurality of the pixels adjacent to each other along a row direction, that are connected to a control terminal of the first switching element in each of the pixels of the corresponding pixel row; a plurality of second scan lines, disposed one for each of the plurality of pixel rows, that are split into a plurality of line-groups and are connected to control terminals of the second switching elements of the pixel groups belonging to each respective group such that, when combining and reading charges from a plurality of pixel groups each configured from a plurality of adjacent pixels in the plurality of pixel rows, charge signals corresponding to combined charge amounts read out from the respective plurality of pixel groups are transmitted through different respective data lines; and a plurality of data lines, disposed so as to respectively intersect with the plurality of first scan lines and the plurality of second scan lines, that transmit first charge signals corresponding to charges read out by the first switching elements in each of the plurality of pixels, and that transmit second charge signals corresponding to the combined charge amounts read by the second switching elements of the respective plurality of pixel groups.

In a third aspect of the present invention, in the second aspect, each of the plurality of pixel groups may be configured from 3 pixels, control terminals of the second switching elements of each of the pixels in respective of the plurality of pixel groups alongside each other in a row direction may be respectively connected to the second scan lines, and adjacent scan lines may be commonly connected as a single line-group.

In a fourth aspect of the present invention, in the third aspect, the 3 pixels may be 3 pixels disposed such that two adjoining sides of each of the pixels are respectively adjacent to one side of each of the other two pixels.

In a fifth aspect of the present invention, in the second aspect, the plurality of pixel groups may be each configured by 4 pixels, the second scan lines may be commonly connected in a line-group configured by an adjacent pair of the second scan lines, each pair of the second scan lines being configured by a second scan line connected to control terminals of the second switching elements of 3 individual pixels in a plurality of respective pixel groups alongside each other in the row direction, and the second scan line connected to the control terminals of the second switching elements of one individual pixel in each of the plurality of pixel groups.

In a sixth aspect of the present invention, in the fifth aspect, the 4 pixels may be configured by 4 pixels made up from 3 pixels disposed such that two adjoining sides of each of the pixels are respectively adjacent to one side of the other 2 pixels out of the 3 pixels, and by 1 pixel may be disposed such that two adjoining sides are respectively adjacent to one side of 2 pixels out of the 3 pixels.

In a seventh aspect of the present invention, in the second to the sixth aspects, the second switching elements may be connected to the plurality of second scan lines are controlled as blocks with shifted timings for each of the line-groups.

In an eighth aspect of the present invention, in the second to the seventh aspects, wherein combinations of the pixels configuring respective pixel groups may be determined such that, when a plurality of hexagonal shaped regions are formed adjacent to each other, the plurality of hexagonal shape regions results in a honeycomb pattern array, wherein each of the hexagonal shape regions may be formed by including inside one center of gravity of a region surrounded by an outline of the plurality of pixel groups configured by the respective 3 pixels or the respective 4 pixels, and by connecting together 6 individual centers of gravity present at the periphery of the one center of gravity.

In a ninth aspect of the present invention, in the above aspects, the hexagonal shaped pixel regions may be formed as regular hexagonal shapes.

In a tenth aspect of the present invention, in the first to the eighth aspects, the hexagonal shaped pixel regions may be formed as flattened hexagonal shapes.

In an eleventh aspect of the present invention, in the tenth aspect, the hexagonal shaped pixel regions may be formed flattened such that one diagonal line out of 3 diagonal lines passing through the center of each of the pixel regions is shorter than the other two diagonal lines and the other two diagonal lines are of equal length to each other In a twelfth aspect of the present invention, in the above aspects, the plurality of data lines may be laid out bent along one portion of the hexagonal shaped pixel region periphery.

In a thirteenth aspect of the present invention, in the above aspects, the sensor portions may include a semiconductor film that receives irradiation with the radiation and generates charges, and the charges may be accumulated in a storage capacitor provided in each of the plurality of pixels and the charges accumulated in the storage capacitor are read by the first switching element and the second switching element.

In a fourteenth aspect of the present invention, in the first to the twelfth aspects, the sensor portions may include a scintillator that converts the radiation that has been irradiated into visible light, and after the converted visible light has been converted into charges by a semiconductor layer, the charges may be read out by the first switching element and the second switching element.

In a fifteenth aspect of the present invention, in the thirteenth aspect, may further include, a plurality of common lines that connect together one electrode of each of the storage capacitors and that fixes the electrodes to a specific electrical potential.

In a sixteenth aspect of the present invention, in the fifteenth aspect, the plurality of common lines may extend between the plurality of data lines in a straight line shape or in a substantially straight line shape.

In a seventeenth aspect of the present invention, in the sixteenth aspect, the plurality of common lines may be connected to the plurality of data lines through the storage capacitors, the first switching elements and the second switching elements.

In an eighteenth aspect of the present invention, in the seventeenth aspect, wherein the plurality of first scan lines, the plurality of second scan lines, the plurality of data lines, the plurality of common lines, the first switching elements, and the second switching elements, are disposed at a lower layer side of the sensor portions.

A nineteenth aspect of the present invention is a radiographic imaging apparatus including: the radiographic image detector of the above aspects; and a radiation irradiation section provided facing the radiographic image detector and that irradiates radiation onto an imaging subject placed above the radiographic image detector, wherein a radiographic image is imaged with the radiographic image detector.

In a twentieth aspect of the present invention, in the nineteenth aspect, the radiation irradiation section may irradiate radiation onto the imaging subject from each of a plurality of different imaging angles.

A twenty-first aspect of the present invention is a radiographic imaging system including: the radiographic imaging apparatus of the above nineteenth and twentieth aspects; and control section that instructs the radiographic imaging apparatus to perform imaging of a radiographic image, and that acquires a radiographic image from the radiographic imaging apparatus, wherein the control section includes, switching section that, based on an external instruction, switches between a first radiographic image acquisition mode that acquires a first radiographic image configured from image data in single-pixel units of a radiographic image detection device, and a second radiographic image acquisition mode that acquires a second radiographic image configured from image data in multi-pixel units of the radiographic image detection device.

In a twenty-second aspect of the present invention, in the twenty-first aspect, when instructed to perform imaging to acquire the second radiographic image, the control section may control the radiation irradiation section such that the radiation amount irradiated onto the imaging subject is an amount according to the multi-pixel unit and smaller than when imaging to acquire the first radiographic image.

A twenty-third aspect of the present invention is a radiographic imaging system including: the radiographic imaging apparatus of the twentieth aspect; control section that instructs the radiographic imaging apparatus to perform imaging of a radiographic image, and that acquires a plurality of radiographic images from the radiographic image detector that have been imaged by the radiographic image detector at each of the imaging angles; and tomographic image generation section that generates a plurality of tomographic images reconstructed with reference to a detection face of the radiographic image detector based on the plurality of radiographic images acquired by the control section; wherein the control section includes, switching section that, based on an external instruction, switches between a first radiographic image acquisition mode that acquires a first radiographic image configured from image data in single-pixel units of a radiographic image detection device, and a second radiographic image acquisition mode that acquires a second radiographic image configured from image data in multi-pixel units of the radiographic image detection device, and wherein the radiation irradiation section has a range of image angles for irradiating radiation onto the imaging subject that is larger when imaging to acquire the first radiographic image than when imaging to acquire the second radiographic image.

In a twenty-second aspect of the present invention, in the twenty-first aspect, the thickness of the tomographic image generated by the tomographic image generation section based on the first radiographic images may be thinner than the thickness of the tomographic images generated based on the second radiographic images.

Thus according to the above aspects, the present invention may image radiographic images at a fast rate, and may maintain even resolution in each of the horizontal, vertical and diagonal directions, before and after charge binning of pixel groups configured by plural pixels.

BRIEF DESCRIPTION OF THE DRAWINGS

Exemplary embodiments of the present invention will be described in detail based on the following figures, wherein.

DETAILED DESCRIPTION OF THE INVENTION

Explanation follows regarding exemplary embodiments of the present invention, with reference to the drawings.

[First Exemplary Embodiment]

Figure 1:
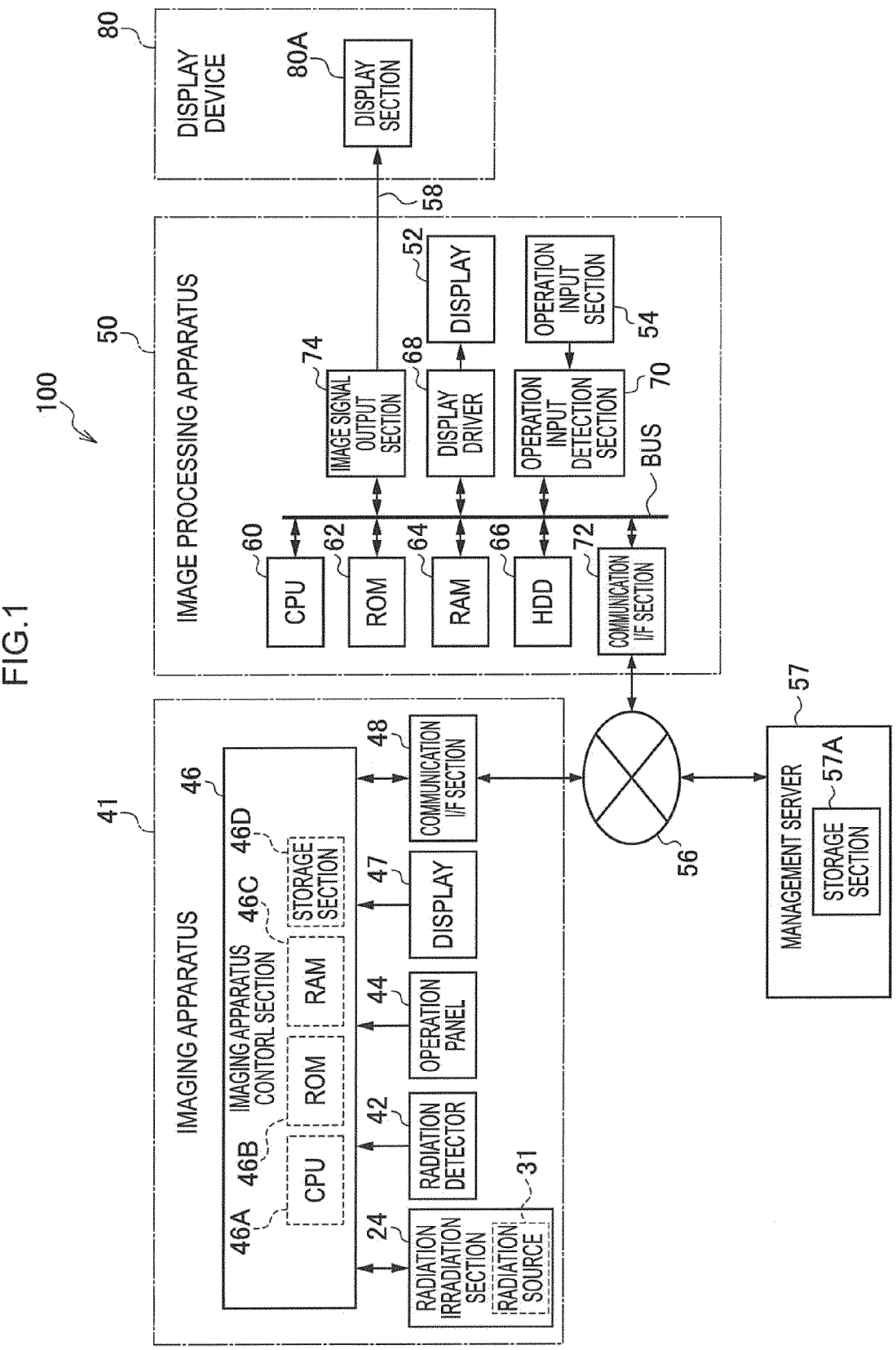
FIG. 1 is a block diagram illustrating a configuration of a radiographic imaging system according to a first exemplary embodiment of the present invention.

FIG. 1 is a block diagram illustrating a configuration of a radiographic imaging system 100 according to a first exemplary embodiment of the present invention. The radiographic imaging system 100 includes an imaging apparatus 41 that images radiographic images, an image processing apparatus 50 that performs image processing on image data expressing imaged radiographic images, and a display device 80 for displaying an image expressed by the image data that has been subjected to image processing.

The imaging apparatus 41 includes a radiation irradiation section 24, a radiation detector 42 that detects a radiographic image, an operation panel 44 that is input with exposure conditions including data, such as, tube voltage, tube current, irradiation duration, imaging conditions, various operation data and various operation instructions, an imaging apparatus control section 46 that controls the operation of the apparatus overall, a display 47 that displays such displays as an operation menu and various information, and a communication I/F section 48 that is connected to a network 56 such as a LAN and that transmits and receives various data to and from other devices connected to the network 56. The imaging apparatus 41 according to the present exemplary embodiment is configured capable of switching between a video imaging mode that successively images radiographic images (video imaging) and a still imaging mode that performs still imaging. The imaging mode can be input as one of the imaging conditions to the imaging apparatus 41 from the operation panel 44. The imaging apparatus 41 performs video imaging or still imaging according to the imaging mode input through the operation panel 44.

The imaging apparatus control section 46 includes a CPU 46A, ROM 46B, RAM 46C and a non-volatile storage section 46D configured, for example, from a HDD or flash memory. The imaging apparatus control section 46 is connected to the radiation irradiation section 24, the radiation detector 42, the operation panel 44, the display 47 and the communication I/F section 48 through a bus (not shown in the drawings). Programs, such as a program for execution by the CPU 46A, are stored in the storage section 46D. Data such as image data (digital data) expressing radiographic images is stored in the storage section 46D. For example, when the imaging apparatus 41 of the present exemplary embodiment is employed for mammography, radiographic image data obtained by imaging the breast of a subject is stored in the storage section 46D.

When irradiated with radiation from the radiation source 31 of the radiation irradiation section 24 according to the exposure conditions, the radiation detector 42 detects the radiation and outputs image data expressing a radiographic image to the imaging apparatus control section 46. Details regarding the configuration of the radiation detector 42 are given later.

The imaging apparatus control section 46 is capable of communicating with the image processing apparatus 50 through the communication I/F section 48 and the network 56, and the imaging apparatus control section 46 performs transmission and reception of various data to and from the image processing apparatus 50. A management server 57 is also connected to the network 56. The management server 57 is configured including a storage section 57A that stores specific management data. The imaging apparatus control section 46 is enabled for communication with the management server 57 through the communication I/F section 48 and the network 56.

The image processing apparatus 50 is configured as a server computer and includes a display 52 that displays for example an operation menu and various data, and an operation input section 54 configured including plural keys for inputting various data and operation instructions. The image processing apparatus 50 includes a CPU 60 for controlling the apparatus operation overall, ROM 62 that is pre-stored with various programs including a control program, RAM 64 for temporary storage of various data, a HDD 66 for storing and retaining various data, a display driver 68 for controlling the display of various data on the display 52, an operation input detection section 70 for detecting operation states with respect to the operation input section 54, a communication I/F section 72 that is connected to the imaging apparatus 41 through the network 56 and that performs transmission and reception of various data to and from the imaging apparatus 41, and an image signal output section 74 that outputs image data through a display cable 58 to the display device 80. The image processing apparatus 50 acquires image data (digital data) expressing radiographic images stored in the storage section 46D from the imaging apparatus 41, via the communication OF section 72.

The CPU 60, the ROM 62, the RAM 64, the HDD 66, the display driver 68, the operation input detection section 70, the communication I/F section 72 and the image signal output section 74 are mutually connected through a system BUS. The CPU 60 is accordingly able to access the ROM 62, the RAM 64 and the HDD 66. The CPU 60 is capable of performing various control, such as controlling display of various data on the display 52 through the display driver 68, controlling transmission and reception of various data to and from the imaging apparatus 41 through the communication I/F section 72, and controlling image display on a display section 80A of the display device 80 through the image signal output section 74. The CPU 60 is also capable of ascertaining user operation states to the operation input section 54 through the operation input detection section 70.

Figure 2:
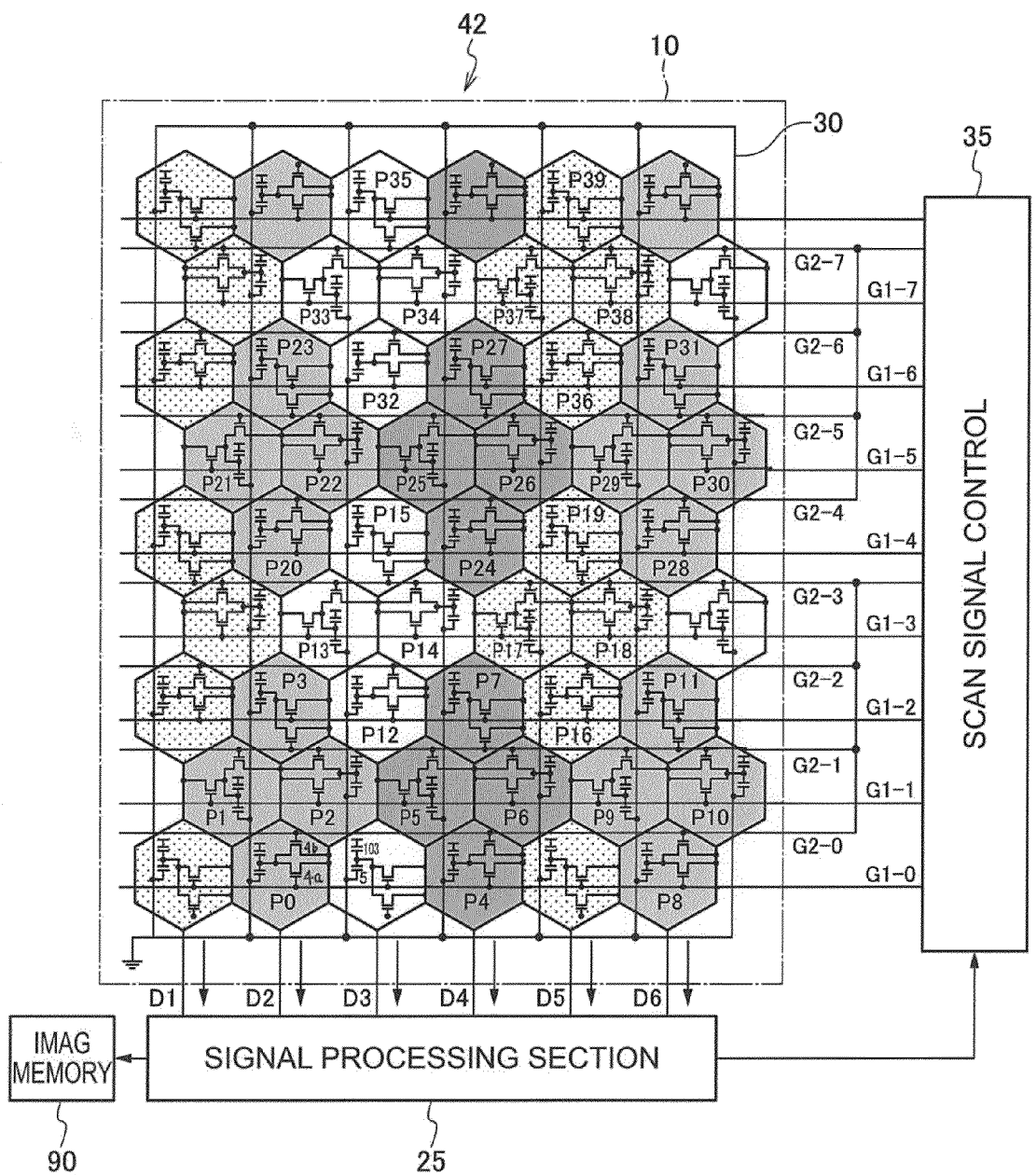
FIG. 2 is a drawing illustrating an electrical configuration of a radiation detector of an imaging apparatus according to the first exemplary embodiment.

FIG. 2 illustrates an electrical configuration of a radiation detector of an imaging apparatus according to the present exemplary embodiment. A radiation detection element 10 of the radiation detector 42 illustrated in FIG. 2 is configured with plural pixels 20 that have hexagonal shaped pixel regions arrayed adjacently in a two dimensional honeycomb pattern, so as to configure a region that is substantially rectangular shaped overall. Each of the pixels 20 is configured including a sensor portion 103 that receives radiation (X-rays) that has been irradiated and generates charges, a charge storage capacitor 5 that accumulates the charges that have been generated in the sensor portion 103, and two thin film transistors (hereinbelow referred to as TFT switches) 4a, 4b for reading the charges accumulated in the charge storage capacitors 5. The radiation detector 42 is accordingly a direct-conversion-type radiation detector that employs a radiation—charge conversion material, such as amorphous selenium in a photoelectric conversion layer, to absorb radiation and convert it into charges, as described later.

Disposing the pixels 20 in a honeycomb pattern means that the pixels 20 having hexagonal shaped pixel regions of the same size as each other are arrayed with plural first pixel rows arrayed in a row direction (the horizontal direction in FIG. 2), and plural second pixel rows, configured by pixels 20 having hexagonal shaped pixel regions of the same size as the first pixel row pixels 20 arrayed in the row direction. The first pixel rows and the second pixel rows are arrayed alternately along a direction that intersects with a column direction (the vertical direction in FIG. 2). The pixels 20 of the second pixel rows are disposed aligned between adjacent pixels of the first pixel rows, such that the pixels 20 of the second pixel rows are displaced in the row direction from the pixels 20 in the first pixel rows by ½ the array pitch of the first pixel row pixels 20.

The radiation detector 42 includes first scan lines G1-0 to G1-7 (also referred to as first scan lines G1, further also referred collectively to as scan lines G when referred together with the below mentioned scan lines) disposed corresponding to each of the pixel rows. The gate electrodes of the TFT switches 4a provided in each of the pixels 20 are connected to the first scan lines G1, and the TFT switches 4a are ON/OFF controlled according to signals flowing in the first scan lines G1. The radiation detector 42 is also equipped with second scan lines G2-0 to G2-3 (also referred to as second scan lines G2) disposed corresponding to each of the pixel rows equipped with the first scan lines G1-0 to G1-3, and with third scan lines G3-0 to G3-3 (also referred to as third scan lines G3) disposed corresponding to each of the pixel rows equipped with the first scan lines G1-4 to G1-7. The gate electrodes of the TFT switches 4b provided in pixels configuring pixel groups, are connected to the second scan lines G2 and the third scan lines G3, and the TFT switches 4b are ON/OFF controlled according to signals flowing in the second scan lines G2 and the third scan lines G3.

Accordingly, the radiation detection element 10 of the radiation detector 42 is configured with pixel rows disposed with one of the first scan lines G1 and one of the second scan lines G2, and with pixel rows disposed with one of the first scan lines G1 and one of the third scan lines G3. The radiation detector 42 is also equipped with plural data lines D1 to D6 (also referred to collectively as data lines D) for reading the charges that were generated in the sensor portions 103 in each of the pixels and accumulated in the respective charge storage capacitors 5, and with common ground lines 30.

Note that the sensor portions 103 of each of the pixels 20 are configured connected to common lines (not shown in the drawings) so as to be applied with a bias voltage from a power supply (not shown in the drawings) through the common lines. Moreover, although FIG. 2 illustrates a configuration in which the second scan lines G2-0 to G2-3 and the third scan lines G3-0 to G3-3 respectively branch from a single line extending out from a scan signal control section 35 into four lines, there is no limitation thereto. For example, configuration may be made such that each of the second scan lines G2-0 to G2-3 and the third scan lines G3-0 to G3-3 extend out separately from the scan signal control section 35, and the second scan lines G2-0 to G2-3 are driven simultaneously and then the third scan lines G3-0 to G3-3 are driven simultaneously.

Configuration may also be made with a second scan signal control section provided separately to the scan signal control section 35, such that 1 line extending out from the second scan signal control section branches into 4. Further, configuration made such that there are separate individual second scan lines G2-0 to G2-3 and third scan lines G3-0 to G3-3 extending out from the second scan signal control section provided separately to the scan signal control section 35, with the second scan lines G2-0 to G2-3 driven simultaneously and the third scan lines G3-0 to G3-3 driven simultaneously. Note that, although the drive load is large in a configuration with a single line branching into 4, there is the advantage that a second scan signal control section does not have to be provided, and a configuration respectively connected to a separate second scan signal control section has the advantage that the drive load is small.

In FIG. 2, for ease of explanation and illustration, an example is shown of a configuration laid out with 14 scan lines G and 6 data lines D. In general, when, for example, there are m×n individual pixels 20 respectively disposed in the row direction and the column direction (wherein m and n are positive integers), there are 2m scan lines and n data lines provided.

In the radiation detector 42, the scan lines G1 to G3 are disposed so as to intersect with the data lines D and the common ground lines 30. The data lines D are laid out along the peripheral edges of the pixels 20 with hexagonal shaped pixel regions in a zigzag pattern (so as to meander) so as to bypass these pixels 20. Namely, the data lines D extend in the column direction while running along 3 adjoining sides out of the peripheral edges (6 sides) of each of the individual pixels 20.

In the radiation detector 45 of the present exemplary embodiment, if, for example, the common ground lines 30 are also disposed in a zigzag pattern (so as to meaner) to match the data lines D, there is the possibility of various issues such as, for example, locations where the separation between TFT switches 4a, 4b in the pixels 20 is narrow occurring at portions meandering to the left or right, common ground lines 30 and TFT switches 4a and 4b colliding, and/or the capacity between data lines D and the common ground lines 30 increasing. The radiation detector 42 of the present exemplary embodiment is therefore, as illustrated in FIG. 2, laid out with the plural scan lines G1 to G3 running along a row direction (the horizontal direction in FIG. 2) arrayed parallel to each other, and the plural data lines D1 to D6 disposed extending along a column direction (the vertical direction in FIG. 2) so as to intersect with the scan lines G1 to G3 and to bend around along the peripheral edges of pixels 20.

The TFT switches 4a, 4b etc., inside each of the pixels 20, are also laid out towards one side so as to secure specific free spaces in each of the pixels 20, and the common ground lines 30 are laid out so as to pass through these free spaces. For example, the TFT switches 4a, 4b etc. are disposed in regions surrounded by a line segment that partitions each of the pixels 20 in half along the column direction (the vertical direction in FIG. 2) and 3 sides at the periphery of each of the pixels 20 where the data lines D are provided. Namely, the TFT switches 4a, 4b etc. are laid out in the region of the right hand half for pixels in a given pixel row, and the TFT switches 4a, 4b etc. are laid out in the region of the left hand half for pixels 20 in the pixel row positioned above and below the given pixel row in the column direction.

Accordingly, the common ground lines 30 may be disposed as straight lines intersecting with the scan lines G1 to G3 between the plural data lines D1 to D6 and without intersecting with the data lines D1 to D6. Hence, the storage capacitor lower electrodes 11 of the charge storage capacitors 5 of each of the pixels 20 can be mutually connected together by the shortest common ground lines 30, in a direct-conversion-type radiographic image detector 42. The need to make the common ground lines 30 meander to match the data lines D is also eliminated. Since there is also no intersection between the data lines D and the common ground lines 30, an increase in noise caused by such effects as induction in the data lines, and an increase in the interline capacitance between the data lines D and the common ground lines 30, may not occur.

The resolution of the radiation detection device can also be raised without the straight line common ground lines 30 impeding higher definition of pixels 20 of the radiation detection element 10. Moreover, in the manufacturing processes for the radiation detection element 10, a drop in manufacturing yield of the radiation detection device due to interline pitch between the data lines D and the common ground lines 30 narrower, may be avoided. Note that, disposing the common ground lines 30 as straight lines means that a straight state is maintained within a range obtainable while allowing for manufacturing error in manufacturing processes of the radiation element 10.

When imaging a radiographic image with the radiation detector 42, during irradiation with external radiation (X-rays) OFF signals are output to the first scan lines G1 and each of the TFT switches 4a is switched OFF, and OFF signals are output to the second scan lines G2 and the third scan lines G3, switching each of the TFT switches 4b OFF. The charges generated in a semiconductor layer are accordingly accumulated in each of the charge storage capacitors 5.

When reading an image, for example a still image, ON signals are output in sequence one line at a time to the first scan lines G1-0 to G1-7, switching the TFT switches 4a in each of the pixels 200N. Or, for example when reading a video image, ON signals are output simultaneously to the second scan lines G2-0 to G2-3 and then ON signals are output simultaneously to the third scan lines G3-0 to G3-3, switching ON the TFT switches 4b of plural pixels in pixel groups. The charges accumulated in each of the charge storage capacitors 5 are thereby read as electrical signals, and a radiographic image is obtained by converting the read electrical signals into digital data.

A signal processing section 25 includes signal detectors (not shown in the drawings) that detect charges flowing out of each of the data lines D1 to D6 as electrical signals, and subjects the detected electrical signals to specific processing. The signal processing section 25 also outputs control signals expressing a signal detection timing to the signal detectors and control signals expressing a scan signal output timing to the scan signal control section 35. As a result, on receipt of the control signals from the signal processing section 25, the scan signal control section 35 outputs signals to the first scan lines G1-0 to G1-7 for switching the TFT switches 4a ON/OFF. The scan signal control section 35 also outputs signals to the second scan lines G2-0 to G2-3 and the third scan lines G3-0 to G3-3 for switching the TFT switches 4b ON/OFF.

The charge signals transmitted by the individual data lines D1 to D3 are amplified in the signal processing section 25 by amplifiers, and are held in sample-and-hold circuits (not shown in the drawings). The charge signals held by the individual sample-and-hold circuits are input in sequence to a multiplexer (not shown in the drawings), and then converted into digital image data by an A/D converter. Note that an image memory 90 is connected to the signal processing section 25, and the digital image data output from the A/D converter is stored in sequence in the image memory 90. The image memory 90, for example, stores digital image data for plural frames worth of imaged radiographic images.

Figure 3:
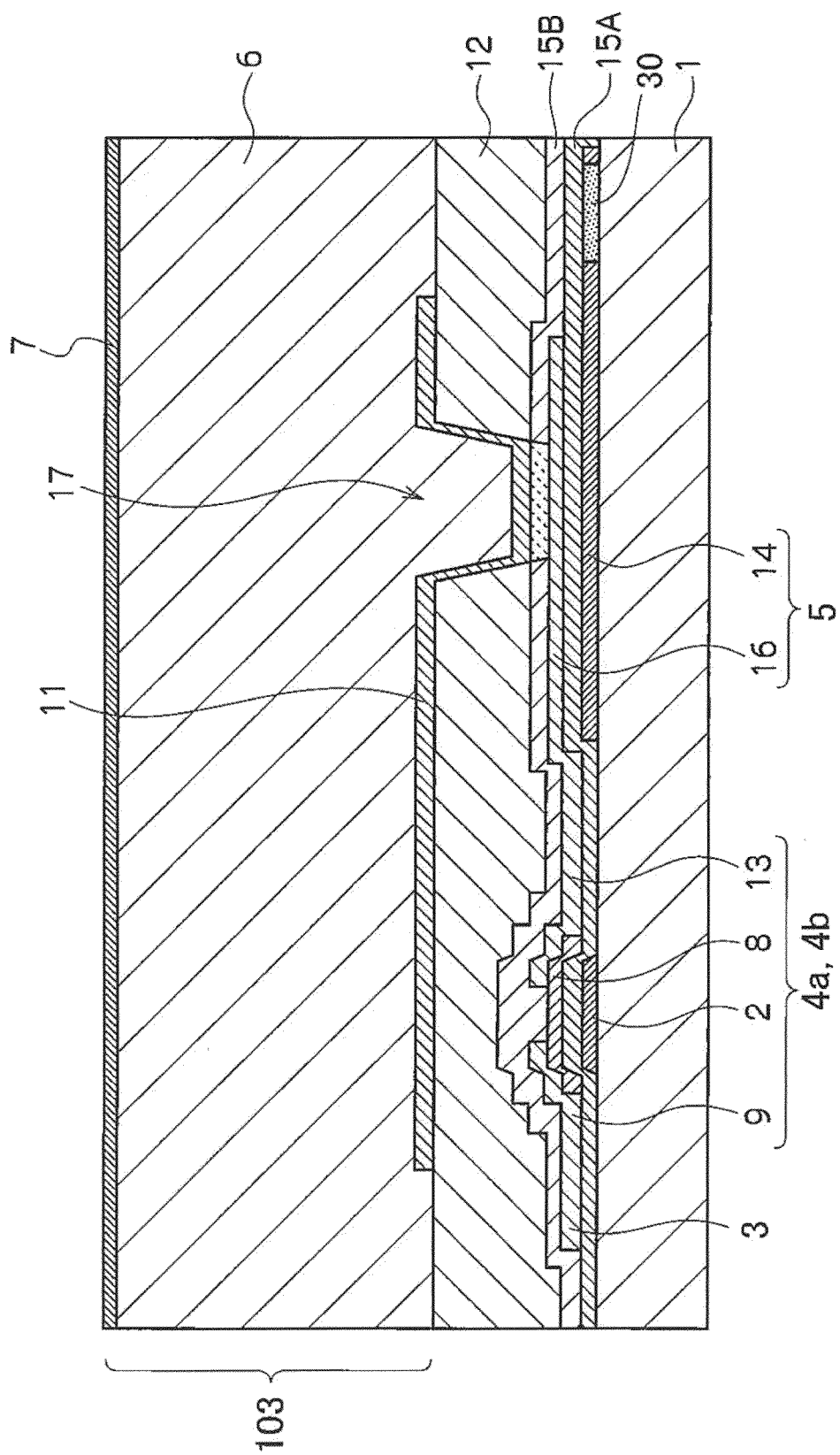
FIG. 3 is a drawing illustrating a partial cross-sectional view of a radiation detection device of a radiation detector according to the first exemplary embodiment.

FIG. 3 illustrates a partial cross-sectional view including a single pixel of a radiation detection element 10 of a radiation detector 42 according to the first exemplary embodiment. The radiation detection element 10 of the radiation detector 42 is, as shown in FIG. 3, a structure in which gate electrodes 2, scan lines G (not shown in FIG. 3) and storage capacitor lower electrodes 14 are formed as a gate wiring layer on an insulating substrate 1. A wiring layer (also referred to as a source wiring layer) formed with source electrodes 9, drain electrodes 13, data lines D, and storage capacitor upper electrodes 16 is formed using a layered film of, for example, Al or Cu, or mainly of Al or Cu. An impurity doped semiconductor layer (not shown in the drawings) such as impurity doped amorphous silicon is formed between semiconductor active layers 8 and the source electrodes 9, and the drain electrodes 13. Note that the source electrodes 9 and the drain electrodes 13 are reversed in the TFT switches 4a, 4b according to the polarity of the charges collected and accumulated by a lower electrode 11.

The gate wiring layer for the gate electrodes 2 is formed using a layered film of, for example, Al or Cu, or mainly of Al or Cu. An insulating film 15A is formed on one face on the gate wiring layer, and the locations of the insulating film 15A above the gate electrodes 2 act as gate insulation films for the TFT switches 4a, 4b. The insulating film 15A is, for example, configured from SiNx, and is formed, for example, by a Chemical Vapor Deposition (CVD) film forming process. The semiconductor active layers 8 are formed with island shapes on the insulation film 15A above each of the gate electrodes 2. The semiconductor active layers 8 are channel portions of the TFT switches 4a, 4b and are, for example, formed from an amorphous silicon film.

The source electrodes 9 and the drain electrodes 13 are formed in a layer above the gate electrodes 2. In the wiring layer in which the source electrodes 9 and the drain electrodes 13 are formed, the data lines D are also formed together with the source electrodes 9 and the drain electrodes 13. The storage capacitor upper electrodes 16 are also formed at positions on the insulating film 15A corresponding to the storage capacitor lower electrodes 14. The drain electrodes 13 are connected to the storage capacitor upper electrodes 16. The data lines D are disposed running along the peripheral edges of the pixels 20 in the manner described above, bent so as to bypass between one pixel and an adjacent pixel. The data lines 3 are connected to the source electrodes 9 formed to the pixels 20 in each of the pixel rows.

A TFT protection layer 15B is formed over substantially the whole surface (substantially all regions) of the region where the pixels are provided on the substrate 1 so as to cover the source wiring layer. The TFT protection layer 15B is formed, for example, from a material such as $SiN_x$ by, for example, a CVD film forming method. A coated interlayer insulating film 12 is then formed on the TFT protection layer 15B. The interlayer insulating film 12 is formed from a low permittivity (specific permittivity $\epsilon_r$=2 to 4) photosensitive organic material (examples of such materials include positive working photosensitive acrylic resin materials with a base polymer formed by copolymerizing methacrylic acid and glycidyl methacrylate, mixed with a naphthoquinone diazide positive working photosensitive agent) at a film thickness of 1 µm to 4 µm.

In the radiation detection element 10 of the radiation detector 42 according to the present exemplary embodiment, intermetal capacitance between metal disposed in the layers above the interlayer insulating film 12 and below the interlayer insulating film 12 is suppressed to be small by the interlayer insulating film 12. Generally the materials of the interlayer insulating film 12 also function as a flattening film, exhibiting an effect of flattening out steps in the layers below. In the radiation detection element 10 of the radiation detector 42, contact holes 17 are formed in the interlayer insulating film 12 and the TFT protection layer 15B at locations corresponding to the storage capacitor upper electrodes 16.

Lower electrodes 11 of each of the sensor portions 103 are formed on the interlayer insulating film 12 for each of the pixels 20, so as to cover the pixel region while also filling each of the contact holes 17. The lower electrodes 11 are formed from an amorphous transparent conducting oxide film (ITO) and are connected to the storage capacitor upper electrodes 16 through the contact holes 17. As a result, the lower electrodes 11 and the TFT switches 4a, 4b are electrically connected through the storage capacitor upper electrodes 16. Note that while the lower electrodes 11 are preferably formed in shapes to match the shapes of the pixel regions of the pixels 20, there is no limitation thereto. For example, when the pixel regions of the pixels 20 are regular hexagonal shaped, the lower electrodes 11 are preferably formed with slightly smaller regular hexagonal shapes so as not to touch the lower electrodes of adjacent pixels. Similarly, when the pixel regions of the pixels 20 are formed in flattened hexagonal shapes the lower electrodes 11 are preferably formed in slightly smaller hexagonal shapes. As long as the pixel placement of the lower electrodes configures a hexagonal lattice, configuration may be made with beveled corner hexagonal shaped or square shaped lower electrodes 11.

A photoelectric conversion layer 6 is uniformly formed on the lower electrodes 11 over substantially the entire surface of the pixel region where the pixels 20 are provided on the substrate 1. The photoelectric conversion layer 6 generates charges (electrons-holes) internally on irradiation with radiation such as X-rays. In other words, the photoelectric conversion layer 6 has electrical conduction properties and is employed to convert image data from radiation into charge data. For example, the photoelectric conversion layer 6 may be formed from amorphous selenium (a-Se) having selenium as the main component and a film thickness of 100 µm to 1000 µm. Note that, the main component means contained at a ratio of 50% of more. An upper electrode 7 is formed on the photoelectric conversion layer 6. The upper electrode 7 is connected to a bias power source (not shown in the drawings) and supplies a bias voltage (for example several kV) from the bias power source. The plural scan lines G1, G2, G3, the data lines 3, the common ground lines 30 and the TFT switches 4a, 4b are disposed at a lower layer side of the sensor portions 103 configured by the photoelectric conversion layer 6.

In the radiation detection element 10 of the radiation detector 42, the gate electrodes 2, the first to the third scan lines G1 to G3 and the storage capacitor lower electrodes 14 are formed as the gate wiring layer on the substrate 1, and the common ground lines 30 are formed on the substrate 1, for example in the same metal layer as the storage capacitor lower electrodes 14.

Explanation next follows regarding operation of the radiation detector 42 according to the present exemplary embodiment. Charges (electron-hole pairs) are generated in the photoelectric conversion layer 6 when X-rays are irradiated onto the photoelectric conversion layer 6 in a state in which a bias voltage is being applied across the upper electrode 7 and the storage capacitor lower electrodes 14. The photoelectric conversion layer 6 and the charge storage capacitors 5 are electrically connected in series, and so electrons generated in the photoelectric conversion layer 6 migrate to the + (plus) electrode side and holes migrate to the − (minus) electrode side.

During image detection, OFF signals (for example, 0V) are output from the scan signal control section 35 to the first scan lines G1-0 to G1-7, the second scan lines G2-0 to G2-3 and the third scan lines G3-0 to G3-3, applying a negative bias to the gate electrodes of the TFT switches 4a, 4b. Each of the TFT switches 4a, 4b are thereby maintained in an OFF state. As a result, electrons generated in the photoelectric conversion layer 6 are collected by the lower electrodes 11, and are accumulated in the charge storage capacitors 5. The photoelectric conversion layer 6 generates a charge amount according to the amount of radiation irradiated, and so the charges according to image data carried by the radiation are accumulated in the charge storage capacitors 5 of each of the pixels. Note that the charge storage capacitors 5 need to be given a larger capacitance than the capacitance formed by the photoelectric conversion layer 6 due to the voltage of several kV referred to above being applied across the upper electrode 7 and the storage capacitor lower electrodes 14.

During image reading, the radiation detector 42 performs in a still imaging mode or a video imaging mode according to instruction from the image processing apparatus 5.0 as described above. When instruction was for the still imaging mode, the signal processing section 25 controls the scan signal control section 35 such that scan signals are output from the second scan lines G2-0 to G2-3 and the third scan lines G3-0 to G3-3 for switching OFF the TFT switches 4b in each of the pixels 20. The signal processing section 25 also controls the scan signal control section 35 to apply ON signals for example with a voltage of +10V to 20V in sequence from the first scan lines G1-0 to G1-7 to the gates of each of the TFT switches 4a in order to switch ON the TFT switches 4a in each of the pixels 20. The TFT switches 4a in each of the pixels 20 are thereby switched to an ON state in sequence for each of the pixel rows, charges are read from the sensor portions 103 by the TFT switches 4a, and signals corresponding to these charges are output to the data lines D.

Thus in the radiation detector 42, in the still imaging mode, in all of the data lines D1 to D6 charge signals flow corresponding to each of the pixels 20 in each of the pixel rows. Accordingly, image data expressing an image representing radiation irradiated onto the radiation detection element 10 of the radiation detector 42 can be obtained. In the signal processing section 25, the charge signals are then converted into digital signals, and a radiographic image based on the image data corresponding to the charge signals is generated.

Explanation follows regarding the video imaging mode. In the radiation detector 42 according to the present exemplary embodiment, out of the plural pixels 20 illustrated in FIG. 2, for example, the 4 pixels P0 to P3 form a pixel group PG0, the 4 pixels P4 to P7 form a pixel group PG1, the 4 pixels P8 to P11 form a pixel group PG2, the 4 pixels P12 to P15 form a pixel group PG3, the 4 pixels P16 to P19 form a pixel group PG4. In these 5 pixel groups, the gate electrodes of each of the TFT switches 4b in, the pixel P0 of the pixel group PG0, the pixel P4 of the pixel group PG1 and the pixel P8 of the pixel group PG2, are connected to the second scan line G2-0. The gate electrodes of each of the TFT switches 4b in, the pixels P1 to P3 of the pixel group PG0, the pixels P5 to P7 of the pixel group PG1, and the pixels P9 to P11 of the pixel group PG2, are connected to the second scan line G2-1.

Similarly, the gate electrodes of each of the TFT switches 4b in, the pixel P12 of the pixel group PG3, and the pixel P16 of the pixel group PG4, are connected to the second scan line G2-2, and the gate electrodes of each of the TFT switches 4b in, the pixels P13 to P15 of the pixel group PG3, and the pixels P17 to P19 of the pixel group PG4, are connected to the second scan line G2-3. In the radiation detection element 10, connections of the pixel groups, (PG5 to PG9) configured by the pixels P20 to P23, the pixels P24 to P27, the pixels P28 to P31, the pixels P32 to P35, and the pixels P36 to P39, and the third scan lines G3-0 to G3-3, are connected in a similar pattern to the connections described above of the pixel groups PG0 to PG4 to the second scan lines G2-0 to G2-3.

When the video imaging mode is instructed to the radiation detector 42, the signal processing section 25 controls the scan signal control section 35 so as to switch OFF the TFT switches 4a of each of the pixels 20, and outputs OFF signals from the first scan lines G1-0 to G1-7 to each of the gate electrodes of the TFT switches 4a of each of the pixels 20.

The signal processing section 25 also controls the scan signal control section 35 to simultaneously drive the second scan lines G2-0 to G2-3 to output scan signals (ON signals). The TFT switches 4b of all the pixels 20 in the pixel groups PG0 to PG4 are switched ON when the ON signal is output simultaneously to the second scan lines G2-0 to G2-3. As a result, the charges accumulated in each of the charge storage capacitors 5 of the four individual pixels P0 to P3 of the pixel group PG0 are combined and the combined charge signal is output to the data line D2. Similarly, a combined charge signal of the four individual pixels P12 to P15 of the pixel group PG3 is output to the data line D3, a combined charge signal of the four individual pixels P4 to P7 of the pixel group PG1 is output to the data line D4, a combined charge signal of the four individual pixels P16 to P19 of the pixel group PG4 is output to the data line D5, and a combined charge signal of the four individual pixels P8 to P11 of the pixel group PG2 is output to the data line D6.

Then the signal processing section 25 controls the scan signal control section 35 to simultaneously drive the third scan lines G3-0 to G3-3 and output scan signals (ON signals) thereto. The TFT switches 4b of all the pixels 20 in the pixel groups PG5 to PG9 are switched ON when the ON signals are simultaneously output to the third scan lines G3-0 to G3-3. As a result a combined charge signal from the four pixels of the pixel group PG5 is output to the data line D2, a combined charge signal of the four pixels of the pixel group PG8 is output to the data line D3, a combined charge signal of the four pixels of the pixel group PG6 is output to the data line D4, a combined charge signal of the four pixels of the pixel group PG9 is output to the data line D5, and a combined charge signal of the four pixels of the pixel group PG7 is output to the data line D6.

Thus, when in the video imaging mode, in each of the plural pixel groups configured by four pre-specified pixels from the plural pixels 20 configuring the radiation detection element 10, the charges accumulated in the four individual pixels are combined (binned) and a charge signal corresponding to the binned charges is output to the respective data lines. This means that when performing video imaging, due to performing binning processing at 2 pixels×2 pixels imaging may be performed at 4 times the rate of the still imaging mode.

As described above, the binning scan lines G (G2 and G3) are split into plural groups (G2 and G3), and scan signals for the TFT switch 4b are sent to the scan lines G belonging to each of the groups at timings shifted for each of the groups. Hence, when combining and reading the charges of the plural pixel groups at each timing, the charge signals corresponding to the combined charge amounts read from different pixel groups are not transmitted through the same data lines D.

Figure 4:
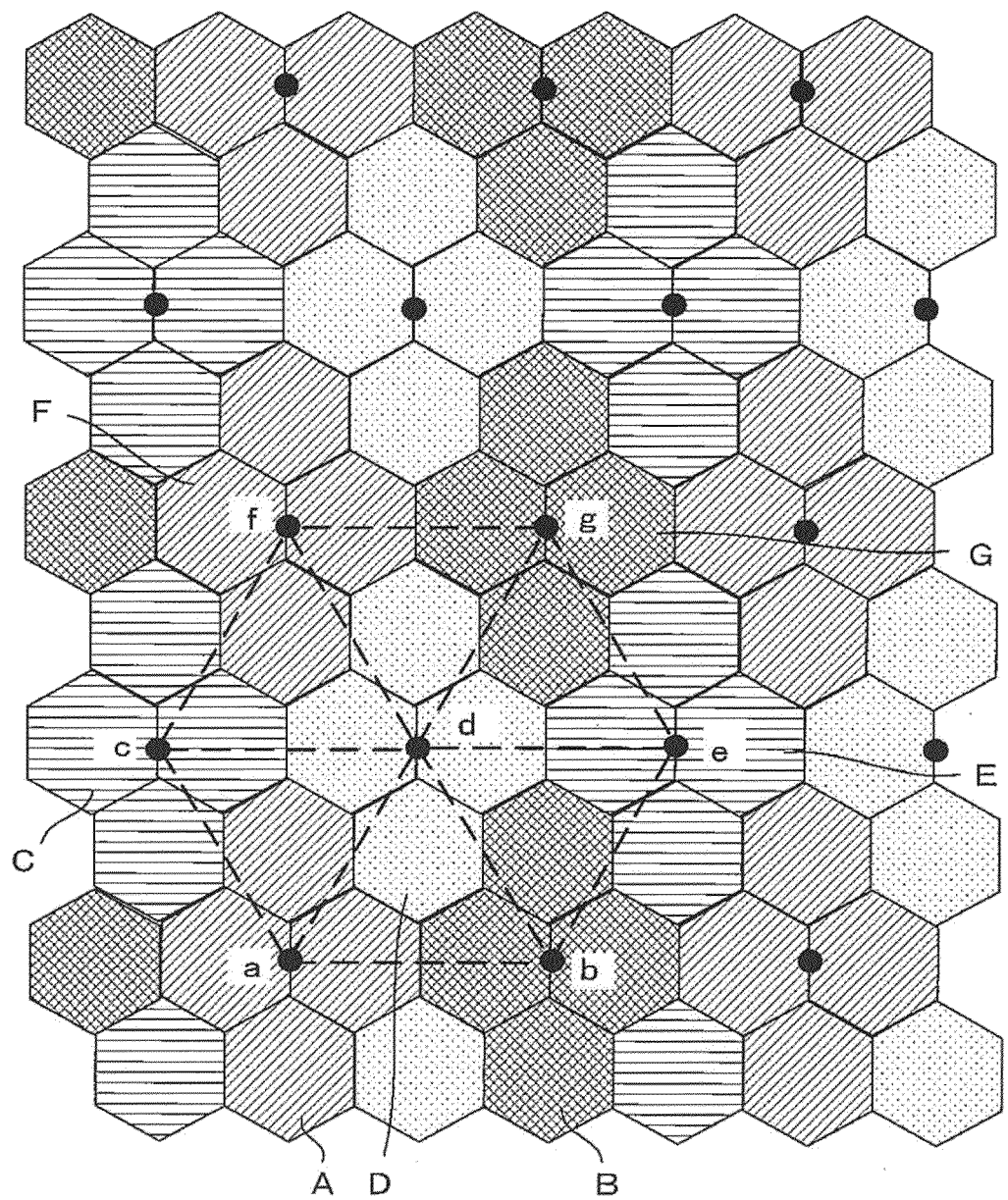
FIG. 4 is a drawing illustrating a layout of pixels and pixel groups subject for binning in the first exemplary embodiment.

FIG. 4 illustrates a layout of pixels and pixel groups subject to binning in the video imaging mode described above. Note that, in FIG. 4, the shading pattern has been changed for each of the pixels in adjacent pixel groups to make it easier to discriminate the respective pixel groups from each other.

In the example illustrated in FIG. 4, the radiation detection element 10 of the radiation detector 42 specifies pixel groups A, B, C, D, E, F, G formed from 4 adjacent pixels as described above. Each of the pixel groups are configured from 4 pixels, configured by a first pixel out of the plural pixels, a second pixel and a third pixel that are each mutually adjacent to each other in a row adjacent to the first pixel row, and a fourth pixel that is in a row adjacent to the second pixel and third pixel row. The 4 pixels are disposed such that two adjoining sides of the first pixel and two adjoining sides of the fourth pixel are respectively adjacent to one side of the second pixel and the third pixel, respectively, so as to lie between the second pixel and the third pixel.

In other words, each of the pixel groups can be defined as being a combination of 4 pixels configured by 3 pixels, disposed such that two adjoining sides of each of the pixels are respectively mutually adjacent to one side of the remaining 2 pixels, and by 1 pixel, disposed such that two adjoining sides are respectively mutually adjacent to one side of 2 pixels out of the 3 pixels. The combination of 4 pixels may also be described as being a combination of 4 pixels formed from 2 pairs of mutually adjacent pixels disposed alongside each other, with 2 adjoining sides of 1 pixel from a first pair disposed mutually adjacent to 1 side of each of the 2 pixels in the other pair respectively.

When still imaging mode is instructed as described above in the radiation detector 42 of the present exemplary embodiment, the signal processing section 25 switches ON the TFT switches 4a in each of the pixels 20 of the radiation detector 42, reads out the charges from each of the pixels, and outputs signals corresponding to the charges to the data lines D. Since pixels with hexagonal shaped pixel regions are employed as the individual pixels in the radiation detection element 10 of the radiation detector 42 of the present exemplary embodiment, a high resolution may be secured in each of the horizontal, vertical and diagonal directions.

However, in the video imaging mode, due to the signal processing section 25 switching ON the TFT switches 4b inside 4 pixels configuring each of the pixel groups as described above, the 4 pixels act as a single pixel, and binning is performed to combine 4 pixels worth of charges. Note that in FIG. 4, the positions of the center of gravity for each of the pixel groups A, B, C, D, E, F, G formed from 4 pixels are positioned as black dots indicated respectively as a, b, c, d, e, f, g.

In the example indicated in FIG. 4, when performing 4 pixel binning for each of the pixel groups, a regular hexagonal shape is formed by connecting the centers of gravity of other pixel groups a-b-e-g-f-c-a, with the center of gravity d of the pixel group D at the center. It can also be seen that the inter center of gravity distances of these pixel groups, namely in the 6 directions d to a, d to b, d to e, d to g, d to f, and d to c, are all the same as each other. Thus by making each of the pixels 20 a hexagonal shape, even resolution may be secured in each of the horizontal, vertical and diagonal directions, before binning. Moreover, since a regular hexagonal shape is also formed by connecting together the centers of gravity of the pixel groups, even resolution may also be secured in each of the horizontal, vertical and diagonal directions, after binning.

Namely, the combinations of each of the pixels in each of the pixel groups are determined such that plural hexagonal shaped regions are arrayed in a honeycomb pattern. By employing, for example, the center of gravity a, b, c, d, e, f, g of each of the regions surrounded by the outlines of the pixel groups A, B, C, D, E, F, G, each of the hexagonal shaped regions are formed including, 1 center of gravity d at the inside, and hexagonal shaped region formed by the line segments connecting the 6 individual centers of gravity a, b, e, g, f, c present at the periphery of the center of gravity d. Accordingly, the present exemplary embodiment may suppress unevenness in each of the horizontal, vertical and diagonal directions of the pixel positions (the center of gravity positions of the pixel groups) after binning, and may enable even resolution to be secured in each of the respective directions, similarly to in an image before binning.

Since the centers of gravity arrayed before binning, and the hexagonal shaped regions formed by the centers of gravity arrayed after binning, are both arrayed in a honeycomb pattern, processing may be performed with a similar algorithm when performing pixel density conversion after binning, to when performing pixel density conversion without binning. Namely, the algorithm for pixel density conversion processing may be commonly employed both before and after binning, without preparing another separate algorithm for pixel density conversion processing after binning. In the image processing apparatus 50 a program for performing pixel density conversion on image data expressing radiographic images detected by the radiation detector 42 is stored on the ROM 62 and/or the HDD 66. The image data output to the display device 80 is accordingly image data after performing pixel density conversion.

Figure 5:
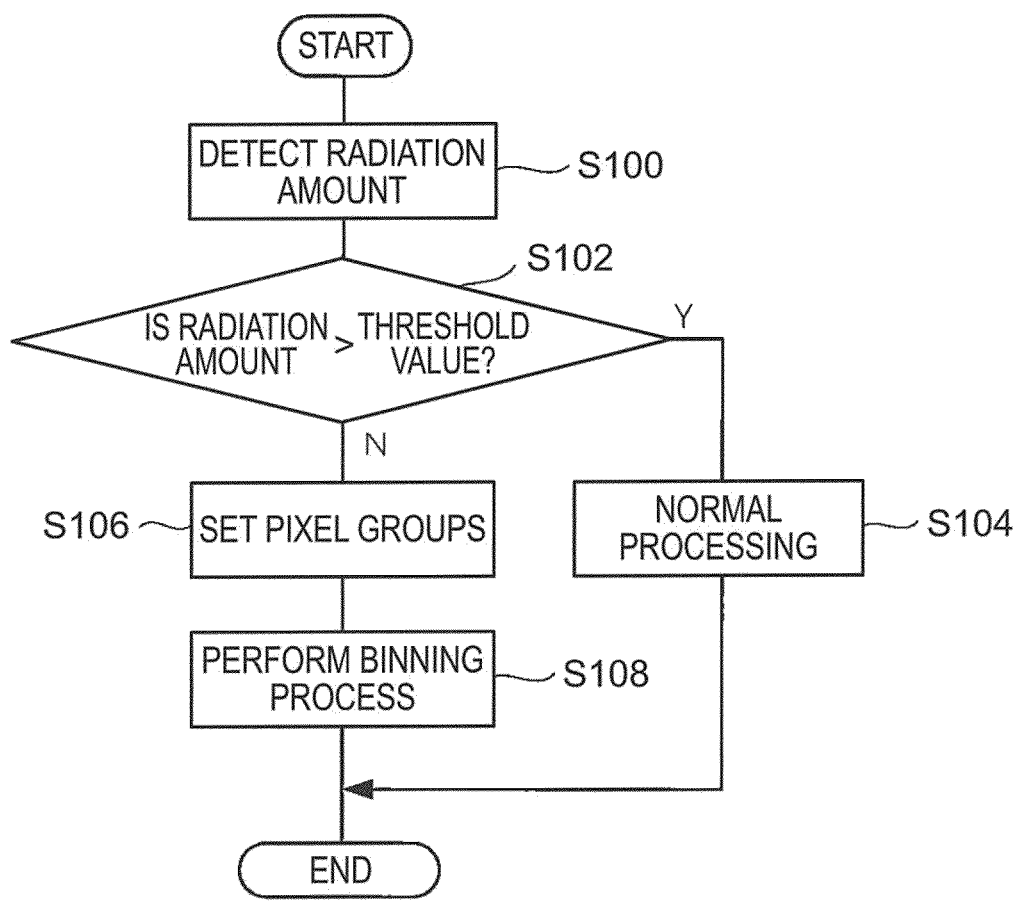
FIG. 5 is a flow chart showing an example of an imaging processing sequence of a radiographic imaging system according the first exemplary embodiment.

FIG. 5 is a flow chart showing an example of an imaging processing sequence executed in the image processing apparatus 50 of a radiographic imaging system 100 according to the present exemplary embodiment. At step S100 of FIG. 5, the amount of radiation irradiated from the radiation irradiation section 24 is detected in the radiation detector 42 of the imaging apparatus 41. Then at step S102 determination is made as to whether or not the radiation amount has exceeded a predetermined threshold value. When determined that the amount of radiation irradiated has exceeded the threshold value, it is determined that sufficient sensitively can be obtained for imaging (image S/N will be sufficient). Processing then proceeds to step S104, ON signals are output in sequence one line at a time to the first scan lines G1-0 to G1-7, scan signals are transmitting to the respective plural pixels 20, and normal processing to read the charge signals accumulated in the storage capacitors 5 of each of the pixels 20 is performed (still imaging mode).

However, when determined at step S102 that the amount of radiation irradiated is the threshold value or lower, it is considered that the S/N for the image obtained would be insufficient, processing proceeds to step S106, and processing is performed to image a high S/N image. Specifically, the pixel groups A, B, C, D, E etc. formed from specific 4 pixels are set as described above. At step S108, scan signals (ON signals) are output by the scan signal control section 35 to the second scan lines G2 and the third scan lines G3 to switch on the TFT switches 4b of each of the pixels disposed in the pixel groups A, B, C, D, E etc., and binning processing is performed to treat the 4 pixels of each of the pixel groups as a single pixel. Thus, if the amount of radiation irradiated is the threshold value or lower, a radiographic image with good S/N is obtained by processing to combine the charges of plural pixels (binning) due to the consideration that otherwise there would be insufficient imaging sensitivity.

Note that, in the imaging process shown in FIG. 5, process is performed in consideration of the S/N of the radiographic image that will be obtained according to the amount of radiation irradiated. However there is no limitation thereto. For example, configuration may be made so as to switch between normal processing without binning and processing with binning according to instruction for the still imaging mode or the video imaging mode, irrespective of the amount of radiation irradiated. Configuration may be made to perform the above switching according to the required resolution for imaging.

Thus, in the present exemplary embodiment, in the radiation detection element 10 of the radiation detector 42, scan lines G1 are disposed for each pixel row connected to the TFT switches 4a in each of the pixels 20 of plural pixels 20 having hexagonal shaped pixel regions arrayed in a honeycomb pattern, and for the predetermined plural pixel groups each configured from 4 pixels, scan lines G2 and G3 are disposed for each pixel row for performing binning processing by reading and combining 4 pixels worth of charges at the same timing. The binning processing scan lines G2 and G3 then output a signal to simultaneously switch ON the TFT switches 4b in the pixels of specific plural pixel groups, and configuration is made such that the charge signals for the combined charges of each of the respective plural pixel groups flow in the separate respective data lines.

By so doing, when binning processing performed by simultaneously reading and combining 4 pixels worth of charges for the plural pixel groups, imaging may be performed at 4 times the rate in comparison to when reading the charge signals from the individual pixels without binning processing. Accordingly, in the present exemplary embodiment, the S/N may be raised by increasing the amount of charge collected, may enable application to a video imaging mode demanding a high frame rate as well as application to low sensitivity images generated by irradiating a small amount of radiation.

Namely, when performing video imaging, the pixel groups configured from 4 pixels are treated as a single pixel, the charges are simultaneously read from plural pixel groups, and binning process is performed to combine the charges accumulated in each of the pixels configuring these pixel groups. Hence, although the resolution is lower than for a still image, a frame rate that is 4 times (a frame duration of 1/4) that of the still imaging mode can be achieved for reading charges successively from each pixel row.

Moreover, combination of 4 pixels in each of the pixel groups is determined such that plural hexagonal shaped regions are arrayed in a honeycomb pattern. Each of the plural hexagonal shaped regions are formed by including inside 1 center of gravity of the region surrounded by the outlines of the pixel groups and the line segments connecting the 6 individual centers of gravity present at the periphery of the 1 center of gravity. Accordingly, unevenness of the pixel positions (the center of gravity position when plural pixels are treated a single pixel clump) after binning in each of the horizontal, vertical and diagonal directions may be suppressed, and even resolution may be secured in each of the respective directions, similarly to in an image before binning.

As a result, a common integrated circuit (IC) may be employed for pixel density conversion before and after binning. Further, processing can be performed employing the same algorithm even in processing by programmable devices such as a FPGA and software rather than with an IC with fixed circuit.

[Second Exemplary Embodiment]

Explanation follows regarding a radiographic imaging system 100 according to a second exemplary embodiment of the present invention. Note that the radiographic imaging system 100 according to the second exemplary embodiment is similar to the radiographic imaging system 100 according to the first exemplary embodiment illustrated in FIG. 1, and so illustration and further explanation will be omitted.

Figure 6:
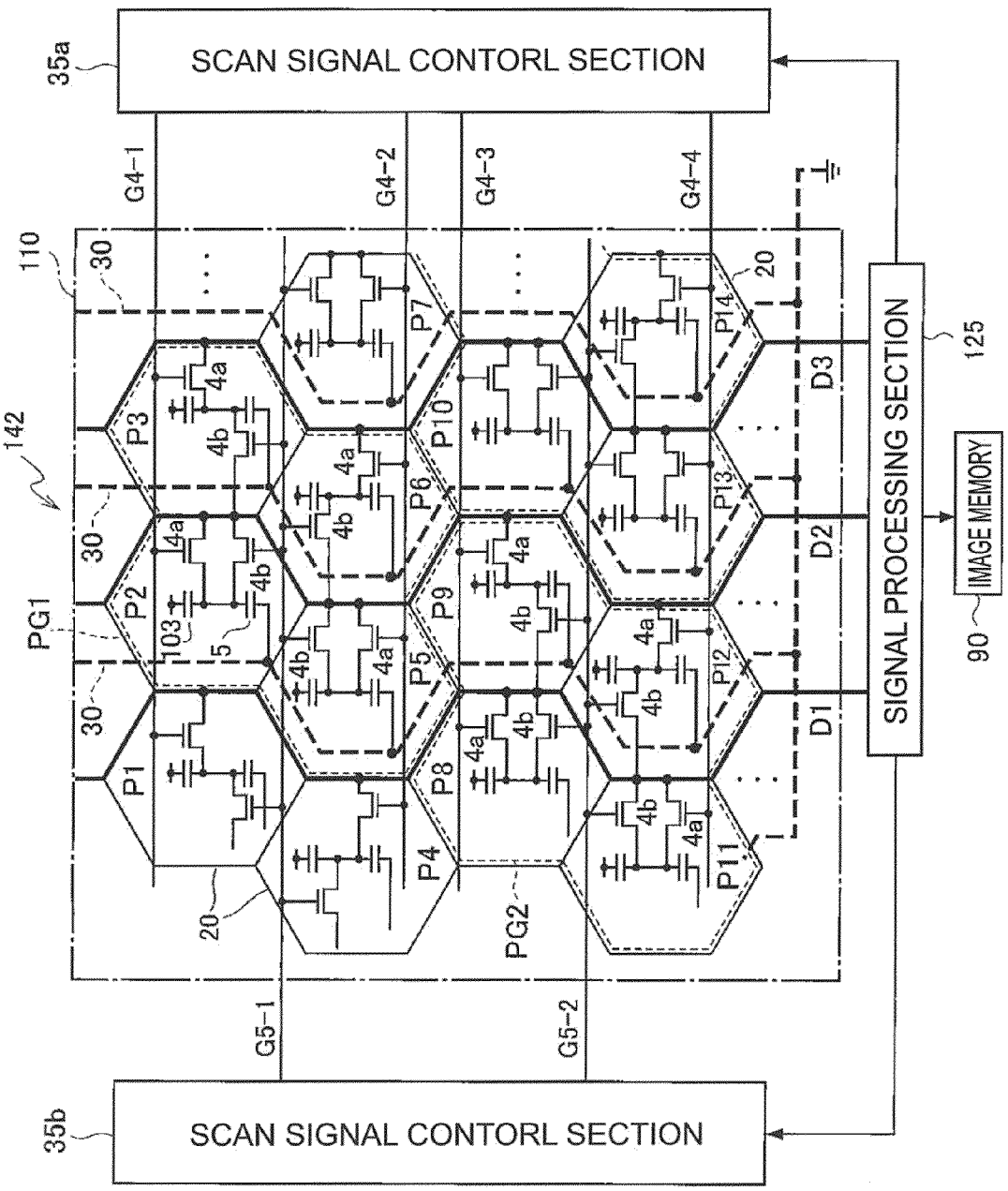
FIG. 6 is a drawing illustrating an electrical configuration of a radiation detector of an imaging apparatus according to a second exemplary embodiment of the present invention.

FIG. 6 illustrates an electrical configuration of a radiation detector 142 in an imaging apparatus 41 of a radiographic imaging system 100 according to the present exemplary embodiment. A radiation detection element 110 of a radiation detector 142 illustrated in FIG. 6 is configured with plural pixels 20 that have hexagonal shaped pixel regions arrayed adjacently in a two dimensional honeycomb pattern, such that the pixels 20 arrayed in a honeycomb pattern configure a rectangular shaped pixel region. Each of the pixels 20 is configured similarly to in the radiation detection element 10 of the radiation detector 42 illustrated in FIG. 2.

The radiation detector 142 includes: fourth scan lines G4-1 to G4-4 (also referred to as fourth scan lines G4) connected to the gate electrodes of the TFT switches 4a provided in each of the pixels 20 for ON/OFF controlling the TFT switches 4a; fifth scan lines G5-1, G5-2 (also referred to as fifth scan lines G5) connected to the gate electrodes of the TFT switches 4b for ON/OFF controlling the TFT switches 4b, plural data lines D1 to D3 (also referred to as data lines D) that read charges generated in sensor portions 103 and accumulated in charge storage capacitors 5; and common ground lines 30.

In FIG. 6, for ease of explanation and illustration, an example is shown of a configuration laid out with 4 lines of the fourth scan lines G4, 2 lines of the fifth scan lines G5, 3 lines of the data lines D, and 3 lines of the common ground lines 30. When, for example, there are m×n individual pixels 20 respectively disposed in the row direction and the column direction (wherein m and n are positive integers), there are m lines of the fourth scan lines G4 and n lines of the data lines D provided. In such cases, the number of the fifth scan lines G5 is half the number of the fourth scan lines G4, namely m/2 lines are provided. The radiation detection element 110 of the radiation detector 142 employs a radiation—charge conversion material such as amorphous selenium, as described later, in a configuration that directly converts radiation to charges. Note that, the common lines (not shown in the drawings) are connected to the sensor portions 103 of each of the pixels 20, in a configuration in which a bias voltage from a power source (not shown in the drawings) is applied through the common lines.

In the radiation detector 142, the scan lines G4, G5 are disposed so as to intersect with the data lines D and the common ground lines 30. The data lines D are laid out along the peripheral edges of the pixels 20 with hexagonal shaped pixel regions in a zigzag pattern (so as to meander) so as to bypass these pixels 20. Namely, the data lines D extend in the column direction while running along 3 adjoining sides out of the peripheral edges (6 sides) of each of the individual pixels 20. The common ground lines 30 are also disposed in a zigzag pattern (so as to meander) so as to keep away from the TFT switches 4a, 4b of each of the pixels 20.

The gate electrodes of the TFT switches 4a are connected to the fourth scan lines G4, and the gate electrodes of the TFT switches 4b are connected to the fifth scan lines G5. One or other of the drain electrodes or the source electrodes of the TFT switches 4a, 4b are connected to one electrode of the charge storage capacitors 5, and the other of the drain electrodes or the source electrodes are connected to the data lines D. When imaging a radiographic image with the radiation detector 142, during irradiation with external radiation (X-rays), OFF signals are output to the fourth scan lines G4 and each of the TFT switches 4a is switched OFF, and OFF signals are output to the fifth scan lines G5, switching each of the TFT switches 4b OFF. Accordingly, the charges generated in a semiconductor layer are accumulated in each of the charge storage capacitors 5.

When reading an image, for example a still image, ON signals are output in sequence one line at a time to the fourth scan lines G4, switching the TFT switches 4a in each of the pixels 20 ON. Or, for example when reading a video image, ON signals are output in sequence one line at a time to the fifth scan lines G5, switching ON the TFT switches 4b of plural pixels in pixel groups. The charges accumulated in each of the charge storage capacitors 5 are thereby read as electrical signals, and a radiographic image is obtained by converting the read electrical signals into digital data.

A signal processing section 125 includes signal detectors (not shown in the drawings) that detect charges flowing out of each of the data lines D1 to D3 as electrical signals, and subjects the detected electrical signals to specific processing. The signal processing section 125 also outputs control signals expressing a signal detection timing and control signals expressing a scan signal output timing respectively to each of the signal detectors and scan signal control sections 35a, 35b. As a result, on receipt of the control signals from the signal processing section 125, the scan signal control section 35a outputs scan signals to the fourth scan lines G4-1 to G4-4 for switching the TFT switches 4a ON/OFF. The scan signal control section 35b also outputs scan signals to the fifth scan lines G5-1, G5-2 for switching the TFT switches 4b ON/OFF.

The charge signals transmitted by the individual data lines D1 to D3 are amplified in the signal processing section 125 by amplifiers and held in sample-and-hold circuits, not shown in the drawings. The charge signals held by the individual sample-and-hold circuits are input in sequence to a multiplexer (not shown in the drawings), and then converted into digital image data by an A/D converter. Note that the digital image data output from the A/D converter is, for example, stored in sequence in the image memory 90 as digital image data for plural frames worth of imaged radiographic images.

Explanation next follows regarding operation of the radiation detector 142 according to the present exemplary embodiment. During image detection with the radiation detector 142, OFF signals (for example, 0V) are output from the scan signal control sections 35a, 35b to the fourth scan lines G4-1 to G4-4 and the fifth scan lines G5-1, G5-2, applying a negative bias to the gate electrodes of the TFT switches 4a, 4b. Each of the TFT switches 4a, 4b are thereby maintained in an OFF state.

During image reading, the radiation detector 142 performs in a still imaging mode or a video imaging mode, according to instruction from an image processing apparatus. When instruction was for the still imaging mode, the signal processing section 125 controls the scan signal control sections 35b such that scan signals are output from the fifth scan lines G5-1, G5-2 for switching OFF the TFT switches 4b in each of the pixels 20. The signal processing section 125 also controls the scan signal control sections 35a to apply ON signals for example with a voltage of +10 V to 20 V in sequence from the fourth scan lines G4-1 to G4-4 to the gates of each of the TFT switches 4a, in order to switch ON the TFT switches 4a in each of the pixels 20. The TFT switches 4a in each of the pixels 20 are thereby switched to an ON state in sequence for each of the pixel rows, charges are read from the sensor portions 103 by the TFT switches 4a, and signals corresponding to these charges are output to the data lines D.

Thus in the radiation detector 142, in the still imaging mode, in each of the data lines D1 to D3 charge signals flow corresponding to each of the pixels 20 in each of the pixel rows. Image data expressing an image representing radiation irradiated onto the radiation detection element 110 of the radiation detector 142 can accordingly be obtained. In the signal processing section 125, the charge signals are then converted into digital signals, and a radiographic image based on the image data corresponding to the charge signals is generated.

Explanation follows regarding the video imaging mode. In the radiation detector 142 according to the present exemplary embodiment, out of the plural pixels 20 illustrated in FIG. 6, for example, the gate electrodes of each of the TFT switches 4b in the 4 pixels P2, P3, P5, P6 surrounded by a dashed line are connected to the fifth scan line G5-1. Similarly, the gate electrodes of each of the TFT switches 4b in the 4 pixels P8, P9, P11, P12 surrounded by a dashed line are connected to the fifth scan line G5-2. The pixels P2, P3, P5, P6 are referred to together as pixel group PG1, and the pixels P8, P9, P11, P12 are referred to together as pixel group PG2. Note that the pixel groups in the radiation detection element 110, while omitted from illustration in FIG. 6, are also configured by plural other pixel groups each formed from 4 specific pixels other than the pixel groups PG1, PG2 (see for example FIG. 7).

When the video imaging mode is instructed to the radiation detector 142, the signal processing section 125 controls the scan signal control section 35a so as to switch OFF the TFT switches 4a of each of the pixels 20, and outputs OFF signals from the fourth scan lines G4-1 to G4-4 to each of the gate electrodes of the TFT switches 4a of each of the pixels 20.

The signal processing section 125 also controls the scan signal control section 35b to sequentially drive the fifth scan lines G5-1, G5-2 to output scan signals (ON signals). Namely, the TFT switches 4b of the four individual pixels P2, P3, P5, P6 of pixel group PG1 are switched ON when the ON signal is output from the fifth scan line G5-1. As a result a combined charge signal summing the charges accumulated in each of the charge storage capacitors 5 of the four individual pixels P2, P3, P5, P6 is output to the data line D2. Then, the TFT switches 4b of the four individual pixels P8, P9, P11, P12 of pixel group PG2 are switched ON when the ON signal is output from the fifth scan line G5-2. In this case a combined charge signal summing the charges accumulated in the four individual pixels P8, P9, P11, P12 is output to the data line D1.

While omitted from illustration in FIG. 6, when the ON signals are output by the fifth scan lines G5-1, G5-2, in the other plural pixels following in the row direction from the pixels of the pixel groups PG1, PG2, charge signals summed in 4 pixel units are also output to data lines similarly to with the pixel groups PG1, PG2.

Thus, when in the video imaging mode, in each of the plural pixel groups configured by four pre-specified pixels that have been bundled together from the plural pixels 20 configuring the radiation detection element 110, the charges accumulated in the four individual pixels are combined (binned), and a combined charge signal corresponding to the binned charges is output to the respective data lines. This means that when performing video imaging, charge signals corresponding to the sum of 2 pixels×2 pixels flow alternately in adjacent data lines D (in FIG. 6 alternately in the even numbered data lines D2 and the odd numbered data lines D1 and D3).

Figure 7:
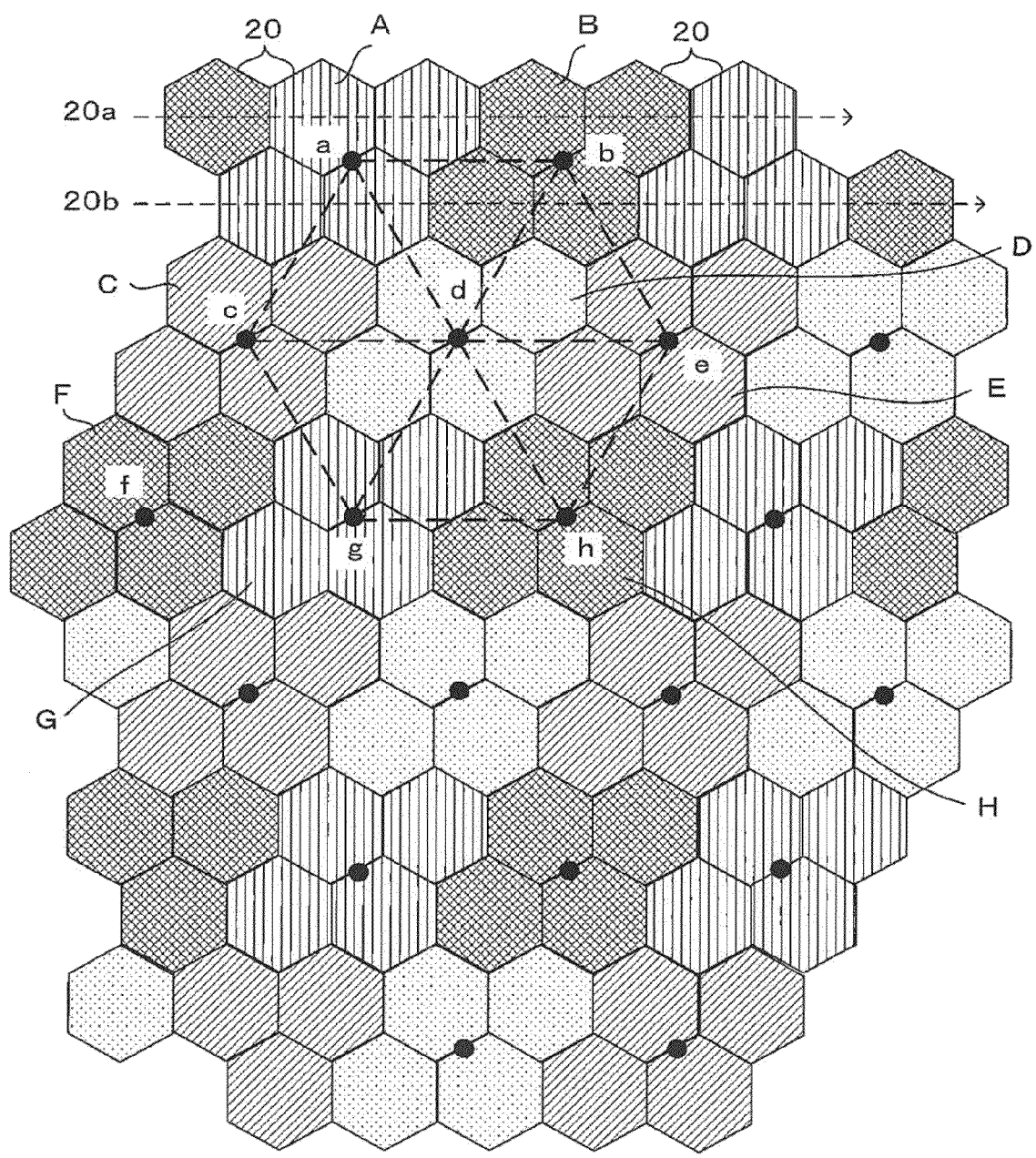
FIG. 7 is a drawing illustrating a layout of pixels and pixel groups subject for binning in the second exemplary embodiment.

FIG. 7 illustrates a layout of pixels and pixel groups subject to binning in the video imaging mode described above. Note that in FIG. 7 the shading pattern is changed in each of the pixels in adjacent pixel groups to make it easier to discriminate the respective pixel groups from each other.

In the example illustrated in FIG. 7, the radiation detection element 110 of the radiation detector 142 specifies pixel groups A, B, C, D, E, F, G, H formed from 4 adjacent pixels as described above. For example, the pixel group A is configured from a total of 4 pixels (the 4 pixels applied with a vertical line pattern), these being 2 adjacent pixels out of the pixels 20 in a first pixel row that is along the row direction appended with 20a in FIGS. 7, and 2 mutually adjacent pixels out of the pixels 20 in a second pixel row positioned in the row below the first pixel row along the row direction appended with 20b in FIG. 7, displaced by ½ the array pitch of the first pixel row to the first 2 pixels.

Each of the pixel groups can be defined as being a combination of 4 pixels configured by 3 pixels disposed such that two adjoining sides of each of the pixels are respectively mutually adjacent to one side of the remaining 2 pixels, and by 1 pixel disposed such that two adjoining sides are respectively mutually adjacent to one side of 2 pixels out of the 3 pixels. The combination of 4 pixels may also be described as being a combination of 4 pixels formed from 2 pairs of mutually adjacent pixels disposed alongside each other, with 2 adjoining sides of 1 pixel from a first pair respectively disposed mutually adjacent to 1 side of each of the 2 pixels in the other pair.

When still imaging mode is instructed, as described above, in the radiation detector 142, the signal processing section 125 switches ON the TFT switches 4a in each of the pixels 20 of the radiation detector 142, reads the charges from each of the pixels, and outputs signals corresponding to the charges to the data lines D. Since pixels with hexagonal shaped pixel regions are employed as the individual pixels in the radiation detection element 110 of the radiation detector 142 a high resolution may be secured in each of the horizontal, vertical and diagonal directions.

However, in the video imaging mode, due to the signal processing section 125 switching ON the TFT switches 4b in the respective 4 pixels configuring each of the pixel groups, the 4 pixels act as a single pixel, and binning is performed to combine 4 pixels worth of charges. The positions of the center of gravity for each of the pixel groups A, B, C, D, E, F, G, H formed from 4 pixels are positioned at the black dots indicated respectively as a, b, c, d, e, f, g, h.

In the example indicated in FIG. 7, when performing 4 pixel binning for each of the pixel groups, a regular hexagonal shape is formed by connecting the centers of gravity a-c-g-h-e-b-a, with the center of gravity d of the pixel group D at the center. It can also be seen that the inter-center of gravity distances of these pixel groups, namely in the 6 directions d to a, d to c, d to g, d to h, d to e, d to b, are all the same as each other. Thus, in the present exemplary embodiment, by making the pixel regions of each of the pixels 20 a hexagonal shape, even resolution may be secured in each of the horizontal, vertical and diagonal directions before binning. Moreover, in the present exemplary embodiment, since a regular hexagonal shape is also formed by connecting together the centers of gravity of the pixel groups, even resolution may also be secured in each of the horizontal, vertical and diagonal directions after binning.

Namely, the combinations of each of the pixels in each of the pixel groups are determined such that plural hexagonal shaped regions are arrayed in a honeycomb pattern. By employing, for example, the centers of gravity a, b, c, d, e, g, h of each of the regions surrounded by the outlines of the pixel groups A, B, C, D, E, F, G, H, each of the hexagonal shaped regions are formed including, 1 center of gravity d at the inside, and hexagonal shaped regions formed by the line segments connecting the 6 individual centers of gravity a, c, g, h, e, b present at the periphery of the center of gravity d. Accordingly, the present exemplary embodiment may suppress unevenness in each of the horizontal, vertical and diagonal directions of the pixel positions (the center of gravity positions of the pixel groups) after binning, and may enable even resolution to be secured in each of the respective directions, similarly to in an image before binning.

Since the centers of gravity arrayed before binning, and the centers of gravity arrayed after binning, both are in a state in which hexagonal shaped regions formed by the centers of gravity are arrayed in a honeycomb pattern, processing may be performed with a similar algorithm when performing pixel density conversion after binning and to when performing pixel density conversion without binning Namely, the algorithm for pixel density conversion processing may be commonly employed both before and after binning, without preparing another separate algorithm for pixel density conversion processing after binning.

Note that, since the imaging processing executed in the imaging apparatus 41 of the radiographic imaging system 100 according to the present exemplary embodiment is similar to the imaging processing executed by the imaging apparatus 41 according to the first exemplary embodiment illustrated in FIG. 5, further explanation thereof is omitted.

Thus, as explained above, in the present exemplary embodiment, for each of the respective predetermined plural pixel groups each configured from 4 pixels out of the plural pixels with hexagonal shaped pixel regions arrayed in a honeycomb pattern in the radiation detector, binning process is performed by simultaneously reading and combining 4 pixels worth of charges, in the radiation detection element 110 of the radiation detector 142. Accordingly, in the present exemplary embodiment, the S/N may be raised by increasing the amount of charge collected, and may enabling application to a video imaging mode demanding a high frame rate as well as application to low sensitivity images generated by irradiating a small amount of radiation.

Moreover, combination of each of the pixels in each of the pixel groups is determined such that plural hexagonal shaped regions are arrayed in a honeycomb pattern. Each of the plural hexagonal shaped regions are formed by including inside 1 center of gravity of the region surrounded by the outlines of the pixel groups and the line segments connecting the 6 individual centers of gravity present at the periphery of the 1 center of gravity. Accordingly, unevenness of the pixel positions (the center of gravity position when plural pixels are treated a single pixel clump) after binning in each of the horizontal, vertical and diagonal directions may be suppressed, and even resolution may be secured in each of the respective directions, similarly to in an image before binning. As a result, a common integrated circuit (IC) may be employed for pixel density conversion before and after binning.

Moreover, when performing video imaging, the pixel groups configured from 2 pixels×2 pixels are read as a single pixel; and binning process is performed combining the charges accumulated in each of the pixels configuring each of the pixel groups. Hence, although the resolution is lower than for a still image, a frame rate can be achieved that is 2 times (a frame duration of 1/2) that for reading charges from each pixel row in the still imaging mode.

Moreover, by thus providing the scan lines G5 for binning, one for each adjacent pair of the pixel rows in the plural pixel rows, the number of scan lines G can be reduced to ½ the number of pixel rows subject to binning, in comparison to cases in which scan lines G are provided one for each of the pixel rows subject to binning. Namely, the number of scan lines G can be greatly reduced in comparison to the radiation detector 42 according to the first exemplary embodiment illustrated in FIG. 2. Moreover, in the configuration of the radiation detector 142 illustrated in FIG. 6, in comparison to the 4 scan lines G1 required when binning is not performed, the total number of scan lines required for scanning the pixels, including performing scanning with binning, has previously been twice the 4 lines, i.e. 8 lines. However, in the present exemplary embodiment only 1.5 times the 4 lines, i.e. 6 lines, are required.

[Third Exemplary Embodiment]

Explanation next follows regarding a radiographic imaging system 100 according to a third exemplary embodiment of the present invention. Note that the radiographic imaging system 100 according to the third exemplary embodiment is similar to the radiographic imaging system 100 according to the first exemplary embodiment illustrated in FIG. 1, and so illustration and further explanation will be omitted.

Figure 8:
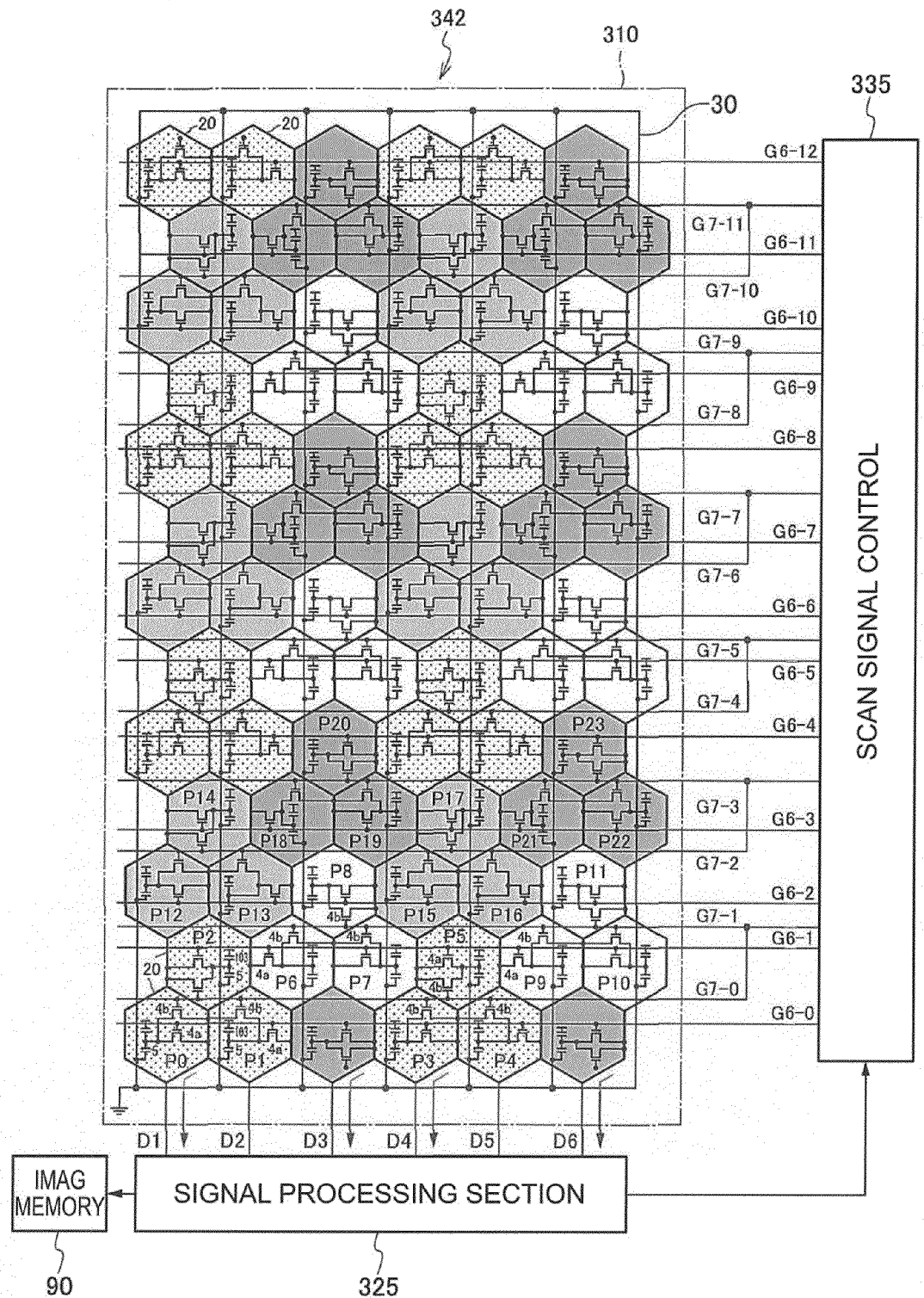
FIG. 8 is a drawing illustrating an electrical configuration of a radiation detector of an imaging apparatus according to a third exemplary embodiment of the present invention.

FIG. 8 illustrates an electrical configuration of a radiation detector 342 in an imaging apparatus 41 according to the third exemplary embodiment. A radiation detection element 310 of a radiation detector 342 illustrated in FIG. 8 is, similarly to the radiation detector 42 according to the first exemplary embodiment illustrated in FIG. 2, configured with plural pixels 20 that have hexagonal shaped pixel regions arrayed adjacently in a two dimensional honeycomb pattern, such that the pixels 20 arrayed in a honeycomb pattern configure a rectangular shaped pixel region.

The radiation detector 342 includes plural scan lines G6-0 to G6-12, G7-0 to G7-11 arrayed parallel to a row direction (the horizontal direction in FIG. 8) and plural data lines D1 to D6 that intersect the scan lines and are provided extending along a column direction (the vertical direction in FIG. 8) bending around the periphery of the pixels 20. For simplicity the scan lines G6-0 to G6-12 are referred to below as sixth scan lines G6 and the scan lines G7-0 to G7-11 are referred to as seventh scan lines G7.

Similarly to in the radiation detector 42 according to the first exemplary embodiment, common ground lines 30 are disposed intersecting with the scan lines G6 and G7 as straight lines between the plural data lines D1 to D6 and without intersecting with the data lines D1 to D6.

Note that, disposing the common ground lines 30 as straight lines means that a straight state is maintained within a range obtainable while allowing for manufacturing error in manufacturing processes of the radiation detection element 310.

Each of the pixels 20 in the radiation detection element 310 is configured including a sensor portion 103 that receives radiation (X-rays) that has been irradiated and generates charges, a charge storage capacitor 5 that accumulates the charges that have been generated in the sensor portion 103, and two TFT switches 4a, 4b for reading the charges accumulated in the charge storage capacitors 5. The radiation detector 342 is accordingly a direct-conversion-type radiation detector 342 that employs a radiation—charge conversion material, such as amorphous selenium, in a photoelectric conversion layer to absorb radiation and convert it into charges.

Explanation follows regarding operation when imaging a radiographic image with the radiation detector 342 according to the third exemplary embodiment. For example, in a still imaging mode, scan signals are output from a scan signal control section 335 to the sixth scan lines G6-0 to G6-12 so as to switch ON the TFT switches 4a in each of the pixels 20 in sequence by pixel row, and scan signals are output from the scan signal control section 335 to the seventh scan lines G7-0 to G7-11 to switch OFF the TFT switches 4b in each of the pixels 20. Accordingly, the charges are read out from the sensor portions 103 in each of the pixels, and signals corresponding to these charges are output to the data lines D1 to D6. Image data expressing images representing radiation that has been irradiated onto the radiation detector 342 is thereby obtained from the charge signals corresponding to each of the pixels 20.

When in video imaging mode, scan signals are output from the scan signal control section 335 to the sixth scan lines G6-0 to G6-12 to switch OFF the TFT switches 4a in each of the pixels 20, and scan signals are output to the seventh scan lines G7-0 to G7-11 to switch ON the TFT switches 4b in each of the pixels 20 as described below.

The radiation detection element 310 of the radiation detector 342 according to the present exemplary embodiment is configured with plural pixel groups respectively configured from 3 predetermined pixels. For example, as shown in FIG. 8, the 3 pixels P0 to P2 form a pixel group PG0, the 3 pixels P3 to P5 form a pixel group PG1, the 3 pixels P6 to P8 form a pixel group PG2, the 3 pixels P9 to P11 form a pixel group PG3, the 3 pixels P12 to P14 form a pixel group PG4, the 3 pixels P15 to P17 form a pixel group PG5, the 3 pixels P18 to P20 form a pixel group PG6, and the 3 pixels P21 to P23 form a pixel group PG7.

Out of the seventh scan lines, the scan line G7-0 is connected to the gate electrodes of each of the TFT switches 4b in the pixels P0 to P2 configuring the pixel group PG0 and the gate electrodes of each of the TFT switches 4b in the pixels P3 to P5 of pixel group PG1. Out of the seventh scan lines, the scan line G7-1 is connected to the gate electrodes of each of the TFT switches 4b in the pixels P6 to P8 configuring the pixel group PG2 and the gate electrodes of each of the TFT switches 4b in the pixels P9 to P11 of pixel group PG3. The scan line G7-0 and the scan line G7-1 are configured as branches of a signal line extending form the scan signal control section 335.

Hence, when a scan signal (ON signal) is output by the scan signal control section 335 to the scan lines G7-0, G7-1, the TFT switches 4b of all of the pixels 20 in the pixel groups PG0 to PG3 are switched ON. As a result the charges accumulated in each of the charge storage capacitors 5 of the 3 individual pixels configuring the respective pixel groups PG0 to PG3 are combined (binned), and the combined charge signal of the pixel group PG0 is output to the data line D1, the combined charge signal of the pixel group PG1 is output to the data line D4, the combined charge signal of the pixel group PG2 is output to the data line D3, and the combined charge signal of the pixel group PG3 is output to the data line D6.

Connections between the each of the TFT switches 4b in each of the pixels configuring the pixel groups PG4 to PG7 and the scan lines G7-2, G7-3 are made in a similar pattern to the connections between the pixel groups PG0 to PG3 and the scan lines G7-0, G7-1 described above. Accordingly, when scan signals (ON signals) are output by the scan signal control section 335 to the scan lines G7-2, G7-3 the TFT switches 4b of all of the pixels 20 in the pixel groups PG4 to PG7 are switched ON. As a result, a combined charge signal (binned signal) of the pixel group PG4 is output to the data line D1, a combined charge signal of pixel group PG5 is output to the data line D4, a combined charge signal of the pixel group PG6 is output to the data line D3, and a combined charge signal of the pixel group PG7 is output to the data line D6.

The above similarly applies to other pixel groups. Specifically, for example, the pixel groups PG8 to PG11 receive scan signals from the scan lines G7-4, G7-5, the pixel groups PG12 to PG15 receive scan signals from the scan lines G7-6, G7-7, the pixel groups PG16 to PG19 receive scan signals from the scan lines G7-8, G7-9, and the pixel groups PG20 to PG23 receive scan signals from the scan lines G7-10, G7-11.

Thus, in the radiation detector 342, when the pixel groups PG0 to PG3, PG8 to PG11, PG16 to PG19 are referred to as even numbered blocks, and when the pixel groups PG4 to PG7, PG12 to PG15, PG20 to PG23 are referred to as odd numbered blocks, charge signals of charges summed in 3-pixel units in the radiation detector 342, alternately for even numbered blocks and odd numbered blocks, flow out into the data lines D1, D3, D4, D6. Charge signals do not flow in the data lines D2, D5 during binning and are in a floating state.

As described above, the binning scan lines G7 are split into plural groups, and scan signals for TFT switches 4b are sent to the scan lines G7 belonging to these groups with timings shifted for each of the groups. Thereby, when combining and reading charges for the plural pixel groups with each timing, charge signals corresponding to combined charge amounts read out from different pixel groups are not transmitted through the same data line.

Note that, for the data lines D2, D5 that are in a floating state during binning process, configuration may be made such that a floating state is avoided by, for example, connecting the source electrodes or the drain electrodes of the TFT switches 4b to the data lines D2, D5 fixed at a specific electrical potential, or connected to lines in the vicinity.

Moreover, whilst in FIG. 8 the scan lines G7-0 to G7-1, G7-2 to G7-3 etc. are configured as 2 branches from a single line respectively extending from the scan signal control section 335. However, there is no limitation thereto. For example, the scan lines G7-0 to G7-1 may be extended separately from the scan signal control section 335 and may be driven simultaneously, and then the scan lines G7-2 to G7-3 may be driven simultaneously. Configuration may also be made with a second scan signal control section provided separately to the scan signal control section 335 in which 1 line extending out from the second scan signal control section branches into 2. Configuration may also be made such that the scan lines G7-0 to G7-3 are extended separately out from the second scan signal control section that is separate to the scan signal control section 335, and the scan lines G7-0, G7-1 are driven simultaneously, and then the scan lines G7-2, G7-3 are driven simultaneously.

In the example illustrated in FIG. 8, for ease of explanation and illustration, an example is shown of a configuration laid out with 25 scan lines G and 6 data lines D. When, for example, there are m×n individual pixels 20 disposed in the row direction and the column direction (wherein m and n are positive integers), 2m scan lines and n data lines D are provided.

Figure 9:
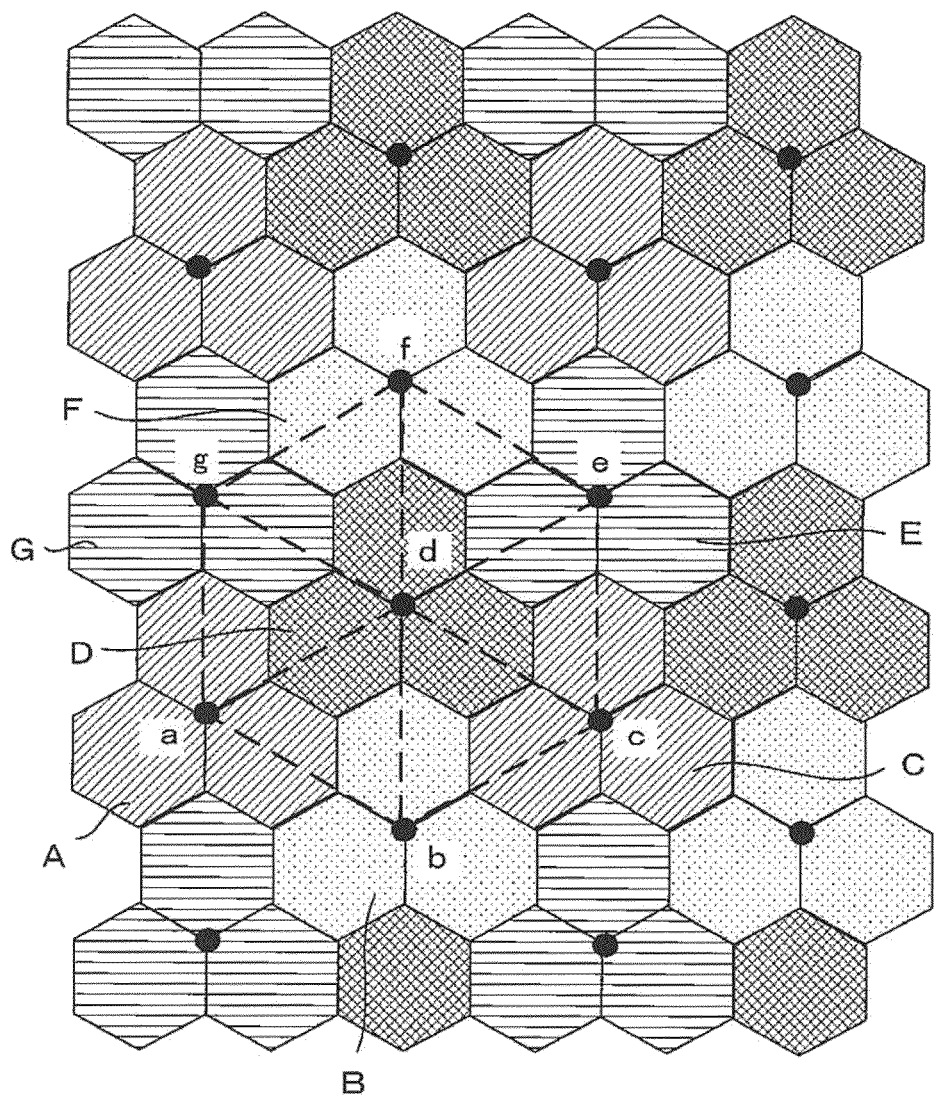
FIG. 9 is a drawing illustrating a layout of pixels and pixel groups subject to binning in the third exemplary embodiment.

FIG. 9 illustrates a layout of pixels and pixel groups subject to binning in the video imaging mode, described above. The shading pattern is again changed for each of the pixels in adjacent pixel groups to make it easier to discriminate the respective pixel groups from each other. In the example illustrated in FIG. 9, the radiation detection element 310 of the radiation detector 342 specifies pixel groups A, B, C, D, E, F, G each formed from adjacent 3 pixels as described above. Each of the pixel groups here is configured by 3 pixels, these being a first pixel out of the plural pixels and 2 other pixels, a second pixel and a third pixel, adjacent to each other in a row adjacent to the first pixel row. The three individual pixels are disposed such that two adjoining sides of the first pixel are respectively adjacent to one side of each of the second pixel and the third pixel. Namely, each of the pixel groups can be defined as being a combination of 3 pixels, made up from 3 pixels disposed such that two adjoining sides of each of the pixels are respectively adjacent to one side of each of the other 2 pixels.

In the radiation detector 342 of the present exemplary embodiment, when the still imaging mode is instructed as described above, the signal processing section 325 switches ON the TFT switches 4a in each of the pixels 20 of the radiation detector 342, reads the charges from each of the pixels, and outputs signals corresponding to the charges to the data lines D. Since pixels with hexagonal shaped pixel regions are employed as the individual pixels in the radiation detection element 310 of the radiation detector 342 a high resolution can be secured in each of the horizontal, vertical and diagonal directions. However, in the video imaging mode, due to the signal processing section 325 switching ON the TFT switches 4b in the respective 3 pixels configuring each of the pixel groups, the 3 pixels act as a single pixel, and binning is performed to combine 3 pixels worth of charges.

In FIG. 9, the positions of the center of gravity for each of the pixel groups A, B, C, D, E, F, G formed from 3 pixels are positioned at the black dots indicated respectively as a, b, c, d, e, f, g. In the example indicated in FIG. 9, when performing 3 pixel binning for each of the pixel groups, a regular hexagonal shape is formed with the center of gravity d of the pixel group D at the center by connecting the centers of gravity a-b-c-e-f-a of the other pixel groups. It can also be seen that the inter center of gravity distances of these pixel groups, namely in the 6 directions d to a, d to b, d to c, d to e, d to f, d to g, are all the same as each other. Thus by making the pixel regions of each of the pixels 20 a hexagonal shape, even resolution may be secured in each of the horizontal, vertical and diagonal directions before binning. Moreover, since a regular hexagonal shape is also formed by connecting together the centers of gravity of the pixel groups, even resolution may also be secured in each of the horizontal, vertical and diagonal directions after binning.

Namely, the combinations of each of the pixels in each of the pixel groups are determined such that plural hexagonal shaped regions are arrayed in a honeycomb pattern. By employing, for example, the center of gravity a, b, c, d, e, f, g of each of the regions surrounded by the outlines of the pixel groups A, B, C, D, E, F, G, each of the hexagonal shaped regions are formed including, 1 center of gravity d at the inside, and hexagonal shaped region formed by the line segments connecting the 6 individual centers of gravity a, b, e, g, f, c present at the periphery of the center of gravity d. Accordingly, the present exemplary embodiment may suppress unevenness in each of the horizontal, vertical and diagonal directions of the pixel positions (the center of gravity positions of the pixel groups) after binning, and may enable even resolution to be secured in each of the respective directions, similarly to in an image before binning.

In the present exemplary embodiment, similarly to in the first exemplary embodiment described above, since the centers of gravity arrayed before binning, and the centers of gravity arrayed after binning, both are in a state in which hexagonal shaped regions formed by the centers of gravity are arrayed in a honeycomb pattern, processing may be performed with a similar algorithm when performing pixel density conversion after binning to when performing pixel density conversion without binning. Hence, the algorithm for pixel density conversion processing may be commonly employed both before and after binning, without preparing another separate algorithm for pixel density conversion processing after binning.

As described above, in the third exemplary embodiment, in the radiation detection element 310 of the radiation detector 342, scan lines G7 are disposed for each pixel row in order to perform binning processing to read and combine respective 3 pixels worth of charges for predetermined plural pixel groups each configured from 3 pixels, and signals are output to specific binning processing scan lines G7 to simultaneously switch ON the TFT switches 4b in each of the pixels of plural pixel groups. Then, configuration is made such that charge scan signals for the charges combined in each of the plural pixel groups flow in separate data lines.

Due to the above configuration, the present exemplary embodiment may simultaneously read and combine 3 pixels worth of charges for the plural pixel groups during binning process, imaging may be performed at 2 times the rate in comparison to when reading out the charge signals from the individual pixels 20 without binning. As a result, the present exemplary embodiment may raise the S/N by increasing the amount of charge collected, enable application to a video imaging mode demanding a high frame rate as well as enabling application to low sensitivity images generated by irradiating a small amount of radiation.

Namely, when performing video imaging, the pixel groups configured from 3 pixels are treated as a single pixel, the charges are simultaneously read from plural pixel groups, and binning processing is performed to combine the charges accumulated in each of the pixels configuring these pixel groups. Hence, although the resolution is lower than for a still image, a frame rate of 2 times (a frame duration of 1/2) that of the still imaging mode for reading charges sequentially from each pixel row may be achieved.

[Fourth Exemplary Embodiment]

Explanation follows regarding a radiographic imaging system 100 according to a fourth exemplary embodiment of the present invention. Note that the radiographic imaging system 100 according to the fourth exemplary embodiment is configured similarly to the radiographic imaging system 100 according to the first exemplary embodiment described above, and so illustration and further explanation will be omitted.

Figure 10:
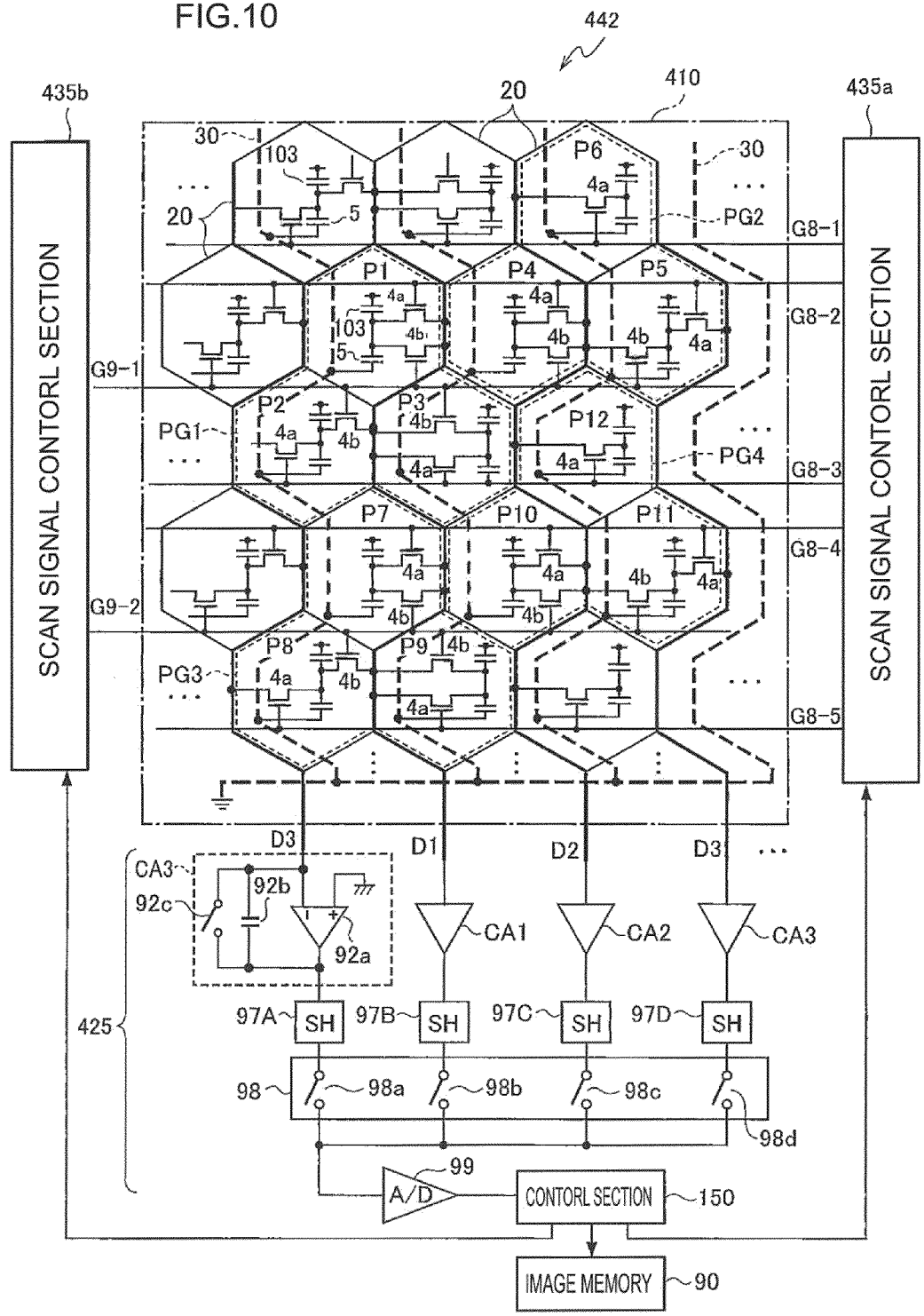
FIG. 10 is a drawing illustrating an electrical configuration of a radiation detector of an imaging apparatus according to a fourth exemplary embodiment of the present invention.

FIG. 10 illustrates an electrical configuration of a radiation detector 442 in an imaging apparatus of a radiographic imaging system 100 according to the fourth exemplary embodiment. A radiation detection element 410 of a radiation detector 442 illustrated in FIG. 10 is, similarly to the radiation detector 42 according to the first exemplary embodiment illustrated in FIG. 2, configured with plural pixels 20 that have hexagonal shaped pixel regions arrayed adjacently in a two dimensional honeycomb pattern, configuring a region that is rectangular shaped overall.

The radiation detector 442 includes: eighth scan lines G8-1 to G8-5 (also referred to as eighth scan lines G8) connected to the gate electrodes of the TFT switches 4a provided in each of the pixels 20 for ON/OFF controlling the TFT switches 4a; ninth scan lines G9-1, G9-2 (also referred to as ninth scan lines G9) connected to the gate electrodes of TFT switches 4b for ON/OFF controlling the TFT switches 4b; plural data lines D1 to D3 (also referred to as data lines D) that read charges generated in sensor portions 103 and accumulated in charge storage capacitors 5; and common ground lines 30.

Note that out of the plural pixels 20, for example pixels P6, P12 and so on each only have the TFT switch 4a as a transistor for reading charges accumulated in the charge storage capacitor 5 in each of the pixels due to the relationship to the timing for reading charges in an imaging mode.

In FIG. 10, for ease of explanation and illustration, an example is shown of a configuration laid out with 5 lines of the eighth scan lines G8, 2 lines of the ninth scan lines G9, 4 lines of the data lines D, and 4 lines of the common ground lines 30. In general when, for example, there are m×n individual pixels 20 respectively disposed in the row direction and the column direction (wherein m and n are positive integers), there are m lines of the eighth scan lines G8 and n data lines provided. The radiation detection element 410 of the radiation detector 442 employs a radiation—charge conversion material such as amorphous selenium that directly converts radiation to charges. Note that the common lines (not shown in the drawings) are connected to the sensor portions 103 of each of the pixels 20 in which a bias voltage from a power source (not shown in the drawings) is applied through the common lines.

In the radiation detector 442, the scan lines G8, G9 are disposed so as to intersect with the data lines D and the common ground lines 30. The data lines D are laid out along the peripheral edges of the pixels 20 with hexagonal shaped pixel regions in a zigzag pattern (so as to meander) so as to bypass these pixels 20. Namely, the data lines D extend in the column direction while running along 3 adjoining sides of the peripheral edges (6 sides) of each of the pixels 20. The common ground lines 30 are also disposed in a zigzag pattern (so as to meaner) so as to keep away from the TFT switches 4a, 4b of each of the pixels 20.

The gate electrodes of the TFT switches 4a are connected to the eighth scan lines G8, and the gate electrodes of the TFT switches 4b are connected to the ninth scan lines G9. One or other of the drain electrodes or the source electrodes of the TFT switches 4a, 4b are connected to one electrode of the charge storage capacitors 5, and the other of the drain electrodes or the source electrodes are connected to the data lines D.

A control section 150 of the radiation detector 442 outputs control signals expressing signal detection timing, and control signals expressing scan signal output timing to scan signal control sections 435a, 435b. On receipt of the control signals from the control section 150, the scan signal control section 435a outputs scan signals to the eighth scan lines G8-1 to G8-5 for switching the TFT switches 4a ON/OFF. The scan signal control section 435b also outputs scan signals to the ninth scan lines G9-1, G9-2 for switching the TFT switches 4b ON/OFF.

When imaging a radiographic image, during irradiation with external radiation (X-rays) OFF signals are output to the eighth scan lines G8 and each of the TFT switches 4a is switched OFF, and OFF signals are output to the ninth scan lines G9, switching each of the TFT switches 4b OFF. The charges generated in a semiconductor layer are accordingly accumulated in each of the charge storage capacitors 5.

When reading an image, for example a still image, ON signals are output in sequence one line at a time to the eighth scan lines G8, switching the TFT switches 4a in each of the pixels 200N. On the other hand, for example when reading a video image, ON signals are output in sequence one line at a time to the ninth scan lines G9, switching ON the TFT switches 4b of plural pixels in pixel groups, described later, and ON signals are output to specific eighth scan lines G8 to switch ON the TFT switches 4a in the pixels 20. The charges accumulated in each of the charge storage capacitors 5 are thereby read as electrical signals, and a radiographic image is obtained by converting the read electrical signals into digital data.

The radiation detector 442 is equipped with variable gain pre-amplifiers (also referred to as charge amplifiers or integrating amplifiers) CA1 to CA3 corresponding to one for each of the data lines D1 to D3, as illustrated in FIG. 10. Sample-and-hold (SH) circuits 97A to 97D are also disposed in the radiation detector 442 at the output side of each of the charge amplifiers CA1 to CA3. The radiation detector 442 is configured with plural data lines disposed in repeating units of data lines D1 to D3, and the plural charge amplifiers are disposed in repeating units of charge amplifiers CA1 to CA3 corresponding thereto. The charge amplifiers CA1 to CA3 are each configured including an operational amplifier 92a with grounded positive input side, a capacitor 92b connected in parallel across the negative input side and the output side of the operational amplifier 92a, and a reset switch 92c. The reset switch 92c is switched by the control section 150. The radiation detector 442 is also equipped with a multiplexor 98 and an analogue to digital (A/D) converter 99.

Note that sampling timings of the sample-and-hold circuit 97A to 97D and selection outputs by switches 98a to 98d provided to the multiplexor 98 are also switched by the control section 150. In FIG. 10, the multiplexor 98 is configured bundling together 4 pixels into 1. However, there is no limitation thereto. For example, the multiplexor 98 may be configured to match the repeating units of the data lines D1 to D3 described above, with 3 pixels bundled into 1.

Explanation next follows regarding operation of the radiation detector 442 according to the present exemplary embodiment. During image detection with the radiation detector 442, OFF signals (for example, 0V) are output from the scan signal control sections 435a, 435b to the eighth scan lines G8-1 to G8-5 and the ninth scan lines G9-1, G9-2, applying a negative bias to the gate electrodes of the TFT switches 4a, 4b. Each of the TFT switches 4a, 4b are thereby maintained in an OFF state.

During image reading, the radiation detector 442 performs imaging in a still imaging mode or a video imaging mode according to instruction from an image processing apparatus 50, as described above. When instruction was for the still imaging mode, the control section 150 controls the scan signal control section 435b such that scan signals are output from the ninth scan lines G9-1, G9-2 for switching OFF the TFT switches 4b in each of the pixels 20. The control section 150 also controls the scan signal control section 435a to apply ON signals for example with a voltage of +10 to 20 V in sequence from the eighth scan lines G8-1 to G8-5 to the gates of each of the TFT switches 4a in order to switch ON the TFT switches 4a in each of the pixels 20. The TFT switches 4a in each of the pixels 20 are thereby switched to an ON state in sequence for each of the pixel rows, charges are read out from the sensor portions 103 by the TFT switches 4a, and signals corresponding to these charges are output to the data lines D.

Thus in the still imaging mode, in the radiation detector 442 charge signals corresponding to each of the pixels 20 flow in each of the data lines D1 to D3 by pixel row. Image data expressing an image representing radiation irradiated onto the radiation detection element 410 of the radiation detector 442 can accordingly be obtained. The charge signals are then converted into digital signals in a signal processing section 425, and a radiographic image based on the image data corresponding to the charge signals is generated.

Figure 11:
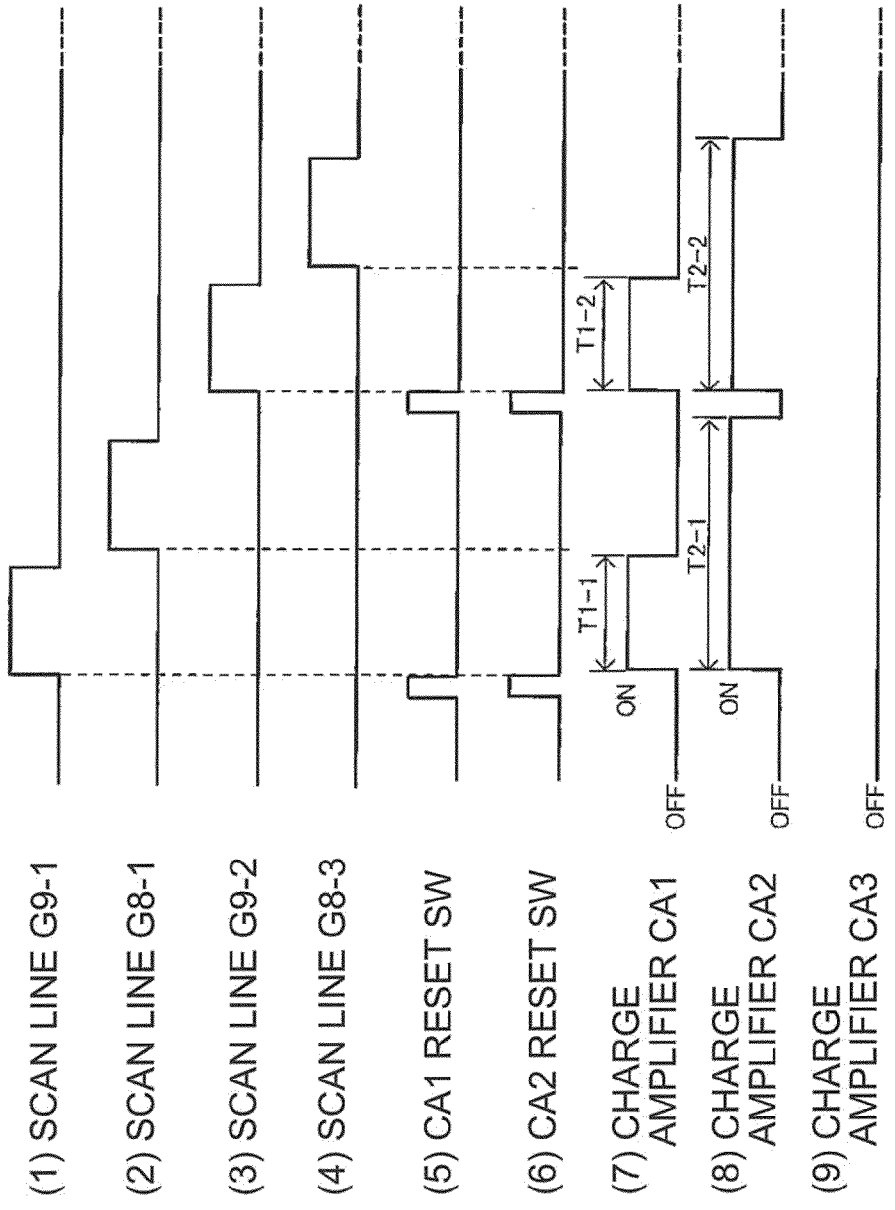
FIG. 11 is an operation timing chart of a radiation detector during binning processing of the fourth exemplary embodiment.

Explanation next follows regarding operation of the video imaging mode in the radiation detector according to the present exemplary embodiment, with reference to an operation timing chart illustrated in FIG. 11. Out of the plural pixels 20 in the radiation detector 442 of the present exemplary embodiment, for example, the gate electrodes of each of the TFT switches 4b disposed in the 3 pixels P1 to P3 surrounded by a dashed line in FIG. 10 are connected to the ninth scan line G9-1. The gate electrodes of the TFT switches 4b disposed in the pixels P4, P5 out of the pixels P4 to P6 likewise surrounded by a dashed line are also connected to the ninth scan line G9-1.

Similarly, the gate electrodes of each of the TFT switches 4b disposed in the pixels P7 to P9 are connected to the ninth scan line G9-2 and the gate electrodes of the TFT switches 4b disposed in the pixels P10, P11 out of the pixels P10 to P12 are also connected to the ninth scan line G9-2.

Here, the pixels P1 to P3 are referred to as pixel group PG1, the pixels P4 to P6 are referred to as pixel group PG2, the pixels P7 to P9 are referred to as pixel group PG3, and the pixels P10 to P12 are referred to as pixel group PG4. Note that, while omitted from illustration in FIG. 10, the radiation detection element 410 is also configured from plural other pixel groups each formed from 3 specific pixels as configuring pixels, mutually adjacent to the pixel groups PG1, PG2 etc. Taking the pixel groups PG1, PG2 as an example, these pixel groups configure pixel group repeating units (each of a total of 6 pixels) with the 3 pixels of the pixel group PG1 (P1 to P3), and 3 pixels made up from 2 pixels of pixel group PG2 (P4, P5) and 1 pixel of pixel group PG2 (P6). The repeating units include 3 successive pixels in the same pixel row direction (in this case P1, P4, P5), 2 successive pixels along a pixel row direction disposed adjacent in the pixel column direction below these 3 successive pixels (in this case P2, P3), and 1 pixel disposed adjacent in the pixel column direction above these 3 successive pixels (in this case P6). Each of the 3 pixels of the respective pixel groups PG1, PG2 are disposed such that two adjoining sides of each of the pixels are respectively adjacent to 1 side of each of the remaining 2 pixels.

In the radiation detector 442 of the present exemplary embodiment, treating the pixels P1 to P6 described above as a single pixel group unit, the radiation detection element 410 is configured by disposing such pixel group units successively along the horizontal and vertical directions of FIG. 10. In other words, in the radiation detector 442, the pixels P1 to P5 and the pixel P12 are treated as a single pixel group unit, and the radiation detection element 410 is configured by disposing such pixel group units successively along the horizontal and vertical directions of FIG. 10.

When the video imaging mode is instructed to the radiation detector 442, the control section 150 initially controls the scan signal control section 435a so as to output OFF signals from the eighth scan lines G8-1 to G8-5 to each of the gate electrodes of the TFT switches 4a of each of the pixels 20 to switch OFF the TFT switches 4a of each of the pixels 20.

The control section 150 then outputs reset signals to short reset switches in the charge amplifiers. For example, as illustrated in (5) and (6) of FIG. 11, reset signals are output to the charge amplifiers CA1, CA2, and the charges accumulated in the capacitors of the charge amplifiers CA1, CA2 are discharged (reset).

The control section 150 then controls the scan signal control section 435b to output scan signals (ON signals) to the ninth scan line G9-1. Specifically, as illustrated in (1) of FIG. 11, an ON signal is output for a specific period of time by the ninth scan line G9-1. The TFT switches 4b of the 3 individual pixels P1 to P3 of the pixel group PG1 are thereby switched ON. As a result, charge signals of the charges that have been accumulated in each of the charge storage capacitors 5 of the pixels P1 to P3 are combined inside the radiation detection element 410, and the combined charge signal of these 3 pixels flows out through the data line D1.

The electrical signal (3 pixels worth of combined charge signal) transmitted by the data line D1 is amplified by a predetermined amplification in the charge amplifier CA1 for a period of time illustrated in (7) of FIG. 11 (referred to as the integration period T1-1), and held in the sample-and-hold circuit 97B. Sampling of the charge signals is stopped as the integration period T1-1 elapses.

When an ON signal is output by the ninth scan line G9-1 ((1) of FIG. 11), the TFT switches 4b in the pixels P4, P5 of the pixel group PG2 are switched ON. As a result, a combined charge signal of charges accumulated in each of the charge storage capacitors 5 of the pixels P4, P5 flows out through the data line D2. The electrical signal (the combined charge signal of pixels P4, P5) transmitted by the data line D2 is amplified by the charge amplifier CA2 for a period of time equivalent to the above integration period T1-1 within the integration period T2-1, as shown at (8) of FIG. 11, and held in the sample-and-hold circuit 97C. The control section 150 ends the integration period T1-1 when the output signal from the ninth scan line G9-1 has changed from ON to OFF, however the integration period T2-1 is continued, in a state in which the charge signals can continue to be accumulated and amplified (integrated) in the charge amplifier CA2.

The control section 150, after switching the output signal from the ninth scan line G9-1 to OFF, then, as illustrated in (2) of FIG. 11, controls the scan signal control section 435a such that the output signal from the eighth scan line G8-1 becomes ON. The TFT switches 4a in the pixels of the pixel row corresponding to the eighth scan line G8-1 are accordingly switched ON, and the charge signals read out from these pixels flow out through each of the data lines. When this occurs, the charge amplifier CA2 is in a state capable of accumulating and amplifying (integrating) the charge signals as described above, however the charge amplifier CA1 is in a non-operational state. Note that in the video imaging mode (during binning driving), since there are no signals flowing through the data lines D3, the control section 150 places the charge amplifier CA3 in a constant non-operational state, as illustrated in (9) of FIG. 11.

Hence, as illustrated in (8) of FIG. 11, in the integration period T2-1 after the period of time of the integration period T1-1 has elapsed, the charge signal of the pixel P6 of the pixel group PG2 flows out through the data line D2, and the charge signal of the pixel P6 is accumulated and amplified (integrated) in the charge amplifier CA2 connected to the data line D2. As a result, in the integration period T2-1 the charge amplifier CA2 adds the charge signal of the pixel P6 to the previously accumulated and amplified (integrated) charge signals of the pixels P4, P5. The combined charge signal of the pixels P4 to P6 are then held in the sample-and-hold circuit 97C, and sampling is ended as the integration period T2-1 elapses.

As described above, when an ON signal is output by the ninth scan line G9-1 and an ON signal is output by the eighth scan line G8-1, similarly to with the pixel groups PG1, PG2, 3 specific pixels worth of combined charge signals are output to data lines in the plural other pixels following in the row direction from the pixels of the pixel groups PG1, PG2.

The control section 150 continues the above processing, and performs binning processing for the pixel groups that are adjacent in the column direction to the pixel groups PG1, PG2 etc. (the pixel groups PG3, PG4 in the example illustrated in FIG. 10). Namely, the control section 150, as illustrated in (5) and (6) of FIG. 11, sends reset signals to the charge amplifiers CA1, CA2 so as to discharge (reset) the charges that have accumulated in the capacitors of these amplifiers. The control section 150, as illustrated in (3) of FIG. 11, controls the scan signal control section 435b so as to output a scan signal (ON signal) with the ninth scan line G9-2. The TFT switches 4b of the 3 individual pixels P7 to P9 of the pixel group PG3 are thereby switched ON, charge signals of charges accumulated in each of the charge storage capacitors 5 of the pixels P7 to P9 are combined in the radiation detection element 410, and a combined charge signal for the 3 pixels (P7 to P9) flows out in the data line D1.

The combined charge signal for 3 pixels is amplified by the charge amplifier CA1 during the integration period T1-2, as illustrated in (7) of FIG. 11, and is held by the sample-and-hold circuit 97B. Then sampling of the charge signal is ended as the integration period T1-2 elapses.

When an ON signal is output by the ninth scan line G9-2, the TFT switches 4b in the pixels P10, P11 of the pixel group 4 are switched ON, and a combined charge signal of the charges accumulated in the pixels P10, P11 flows out in the data line D2. The combined charge signal is amplified by the charge amplifier CA2 for a period of time equivalent to the integration period T1-2 within the integration period T2-2, as illustrated in (8) of FIG. 11, and is held in the sample-and-hold circuit 97C. In this case too, the control section 150 ends the integration period T1-2 when the output signal from the ninth scan line G9-2 has become OFF, but the integration period T2-2 is not ended, and a state continues in which the charge signal can continue to be accumulated and amplified (integrated) in the charge amplifier CA2.

After the output signal from the ninth scan line G9-2 has become OFF, as illustrated in (4) of FIG. 11, the output signal from the eighth scan line G8-3 is switched ON. The TFT switches 4a in the pixels of the pixel row corresponding to the eighth scan line G8-3 are thereby switched ON. When this occurs, the charge amplifier CA1 is not in an operational state, however the charge amplifier CA2 is maintained in a state capable of accumulating and amplifying (integrating) the charge signals, as described above. Note that, as described above, in video imaging mode (during binning driving) signals do not flow in the data line D3. Consequently, as illustrated in (9) of FIG. 11, the charge amplifier CA3 is constantly in a non-operational state during binning driving.

Hence, as illustrated in (8) of FIG. 11, for the period of time of the integration period T2-2 after the integration period T1-2 has elapsed, the charge signal of the pixel P12 of the pixel group PG4 flows in the data line D2, and the charge signal of the pixel P12 is accumulated and amplified (integrated) in the charge amplifier CA2 connected to the data line D2. As a result, in the charge amplifier CA2, during the integration period T2-2 the charge signal of the pixel P12 is added to the charge signals of the pixels P10, P11 previously accumulated and amplified (integrated) in the charge amplifier CA2. Then, the combined charge signal for the pixels P10 to P12 is held in the sample-and-hold circuit 97C, and sampling is ended as the integration period T2-2 elapses.

When ON signals are output by the ninth scan line G9-2 and the eighth scan line G8-3, similarly to with the pixel groups PG3, PG4, 3, specific pixels worth of combined charge signals are output to data lines from the plural other pixels following in the row direction from the pixel groups PG3, PG4.

By the control section 150 driving the sample-and-hold circuits 97A to 97D for specific periods of time, the signal levels of the electrical signals that have been amplified by the variable gain charge amplifiers CA1 to CA3 are held in the sample-and-hold circuits. The charge signals respectively held in the individual sample-and-hold circuits are, after being selected in sequence by the multiplexer 98, converted into digital image data by the A/D converter 99. Note that the digital image data output from the A/D converter 99 is stored in sequence in an image memory 90. The image memory 90, for example, stores plural frames worth of imaged radiographic images as digital image data.

Note that while not illustrated in FIG. 10, when ON signals are output by the ninth scan lines G9-1, G9-2, similarly to with the pixel groups PG1, PG2, charge signals summed in 3 pixel units are output to the data lines from the plural other pixels following in the row direction from the pixel groups PG1, PG2.

Thus, in the video imaging mode, in the respective plural pixel groups configured by bundles of 3 pre-specified pixels from the plural pixels configuring the radiation detection element 410, the charges accumulated in the 3 individual pixels are combined (binned) and charge signals corresponding to the charges combined through binning are output to the data lines. Then after controlling the ninth scan lines G9, by outputting ON signals from the odd numbered scan lines (G8-1, G8-3 etc.) out of the eighth scan lines G8 in FIG. 10, the charge signals of the remaining single pixels, in the pixel groups for which 2 pixels worth of combined charge signals have already been acquired, flow in the data lines. In the video imaging mode, an OFF signal is constantly output from the even numbered scan lines (G8-2, G8-4 etc.) out of the eighth scan lines G8.

Consequently, in the radiation detector according to the present exemplary embodiment, 3-pixel binning processing is performed for the pixels of specific pixel groups (PG2, PG4 etc.) by employing the same charge amplifier to add together and combine 2 pixels worth of the charge signals out of the 3 pixels configuring each of the pixel groups, and then the charge signal of the remaining 1 pixel using shifted integration timings.

Note that, also in the video imaging mode of the radiation detector 442 according to the present exemplary embodiment, similarly to in the radiation detector 342 according to the third exemplary embodiment illustrated in FIG. 8, taking the center of gravity of one pixel group out of the pixel groups configured from 3 pixels as the center, a regular hexagonal shape is formed by connecting together the centers of gravity of the other pixel groups, and the inter-center of gravity distances of these pixel groups are all the same as each other in 0.6 directions. Thus, in the present exemplary embodiment, even resolution may be secured in each of the horizontal, vertical and diagonal directions in before and after binning. Thus, in the present exemplary embodiment, unevenness in the pixel positions (the center of gravity positions of the pixel groups) may be suppressed after binning, enabling even resolution to be secured in each of the respective directions, similarly to in an image before binning.

Thus in the present exemplary embodiment, since the centers of gravity arrayed before binning, and the centers of gravity arrayed after binning, both are in a state in which hexagonal shaped regions formed by the centers of gravity are arrayed in a honeycomb pattern, processing may be performed with a similar algorithm when performing pixel density conversion after binning to when performing pixel density conversion without binning. Hence, the algorithm for pixel density conversion processing may be commonly employed both before and after binning, without preparing a separate algorithm for pixel density conversion processing after binning.

In the present exemplary embodiment, for each of the respective predetermined plural pixel groups each configured from 3 pixels out of the plural pixels with hexagonal shaped pixel regions arrayed in a honeycomb pattern in the radiation detector 442, binning process is performed by simultaneously reading and combining 3 pixels worth of charges in the radiation detection element 410 of the radiation detector 442. Moreover 3-pixel binning process is performed for specific pixel groups, by employing the same charge amplifier to add together 2 pixels worth of the charge signals out of the 3 pixels configuring each of the pixel groups, and then the charge signal of the remaining 1 pixel using shifted integration timings. Accordingly, in the present exemplary embodiment, the S/N may be by increasing the amount of charge collected, and may enable application to a video imaging mode demanding a high frame rate as well as application to low sensitivity images generated by irradiating a small amount of radiation.

Moreover, combination of each of the pixels in each of the pixel groups is determined such that plural hexagonal shaped regions are arrayed in a honeycomb pattern. Each of the plural hexagonal shaped regions are formed by including inside 1 center of gravity of the region surrounded by the outlines of the pixel groups, and the line segments connecting the 6 individual centers of gravity present at the periphery of the 1 center of gravity. Accordingly, unevenness of the pixel positions (the center of gravity position when plural pixels are treated a single pixel clump) after binning in each of the horizontal, vertical and diagonal directions may be suppressed, and even resolution may be secured in each of the respective directions, similarly to in an image before binning. As a result, a common integrated circuit (IC) may be employed for pixel density conversion before and after binning.

Moreover, when performing video imaging, charges are acquired by treating each of the pixel groups configured from 3 respective pixels as a single pixel, and binning process is performed by combining the charges accumulated in each of the pixels configuring each of the pixel groups. Hence, although the resolution is lower than for a still image, a frame rate of 2 times (a frame duration of 1/2) that for reading charges from each pixel row may be achieved in the still imaging mode. Moreover, the number of scan lines G9 can be reduced to ½ the number of pixel rows subject to binning, in comparison to cases in which scan lines G9 are provided one for each of the pixel rows subject to binning. Namely, the number of scan lines G may be greatly reduced in comparison to the radiation detector 342 according to the third exemplary embodiment illustrated in FIG. 8. Moreover, in the configuration of the radiation detector 442 illustrated in FIG. 10, in comparison to the 5 scan lines G8 required when binning is not performed, the total number of scan lines required for scanning the pixels, including performing scanning with binning, has previously been twice the 5 lines, i.e. 10 lines. However, in the present exemplary embodiment only 7 lines are required.

In each of the above exemplary embodiments, the hexagonal shaped pixels of the radiation detection element 410 may include regular hexagonal shaped pixels and substantially hexagonal shaped pixels that have their corners beveled. Moreover, for example, flattened hexagonal shaped pixels squashed in the top-bottom direction on the page of FIG. 2, and substantially hexagonal shaped pixels when viewed in plan view may also included. Namely, configuration may be made with pixels having hexagonal shaped pixel regions formed flattened such that one diagonal line out of 3 diagonal lines passing through the center of each of the pixels is shorter than the other two diagonal lines and the other two diagonal lines are of equal length to each other. Thus even though pixels of flattened hexagonal shape are employed, the relationships of the center of gravity separations and the six horizontal, vertical and diagonal directions may be maintained before and after binning processing.

In each of the above exemplary embodiments, explanation has been given of cases in which the present invention is applied to a direct-conversion-type radiation detector 410 employing a radiation—charge conversion material such as amorphous selenium in a photoelectric conversion layer that absorbs radiation and converts the radiation into charge. However, the present invention is not limited thereto. For example, the present invention may be applied to an indirect-conversion-type radiation detector equipped with a scintillator that converts irradiated radiation into visible light.

Figure 12:
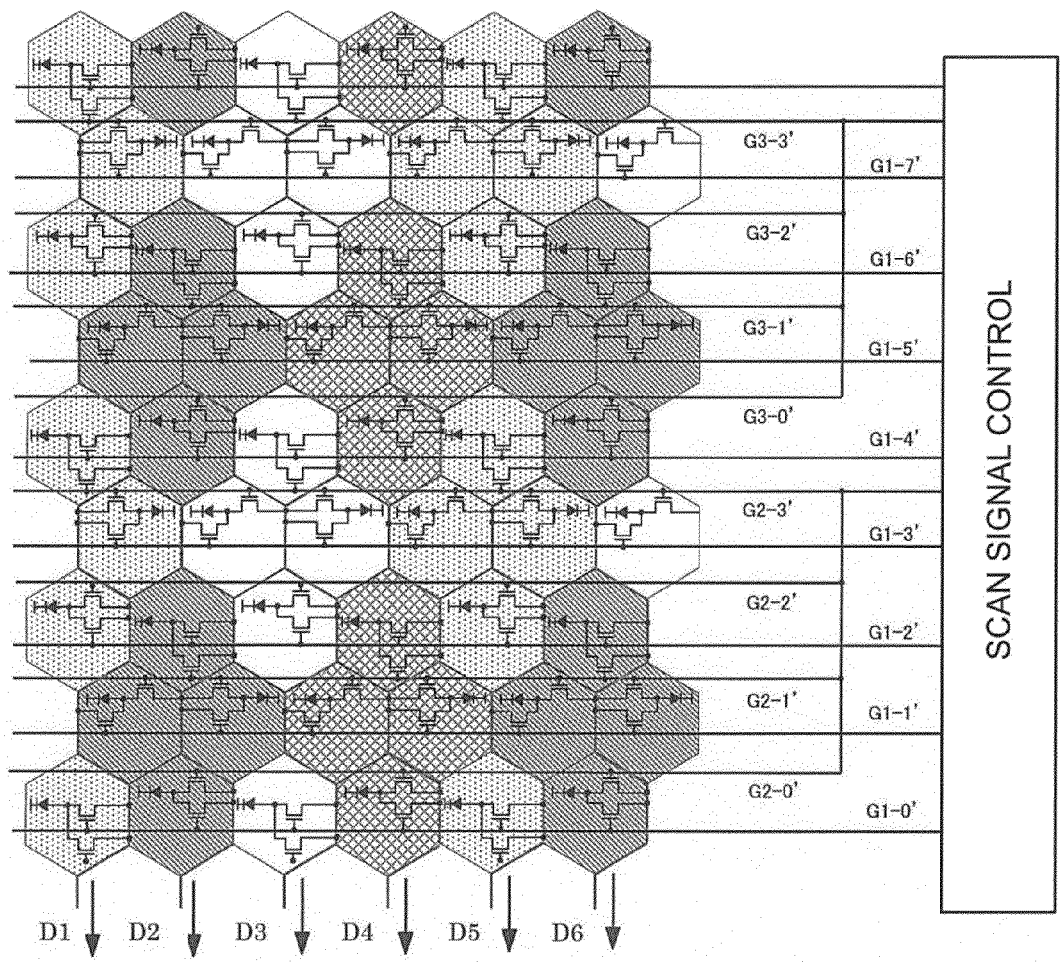
FIG. 12 is a drawing illustrating a simplified example of a radiation detector of the first exemplary embodiment applied to an indirect-conversion-type radiation detector.
Figure 13:
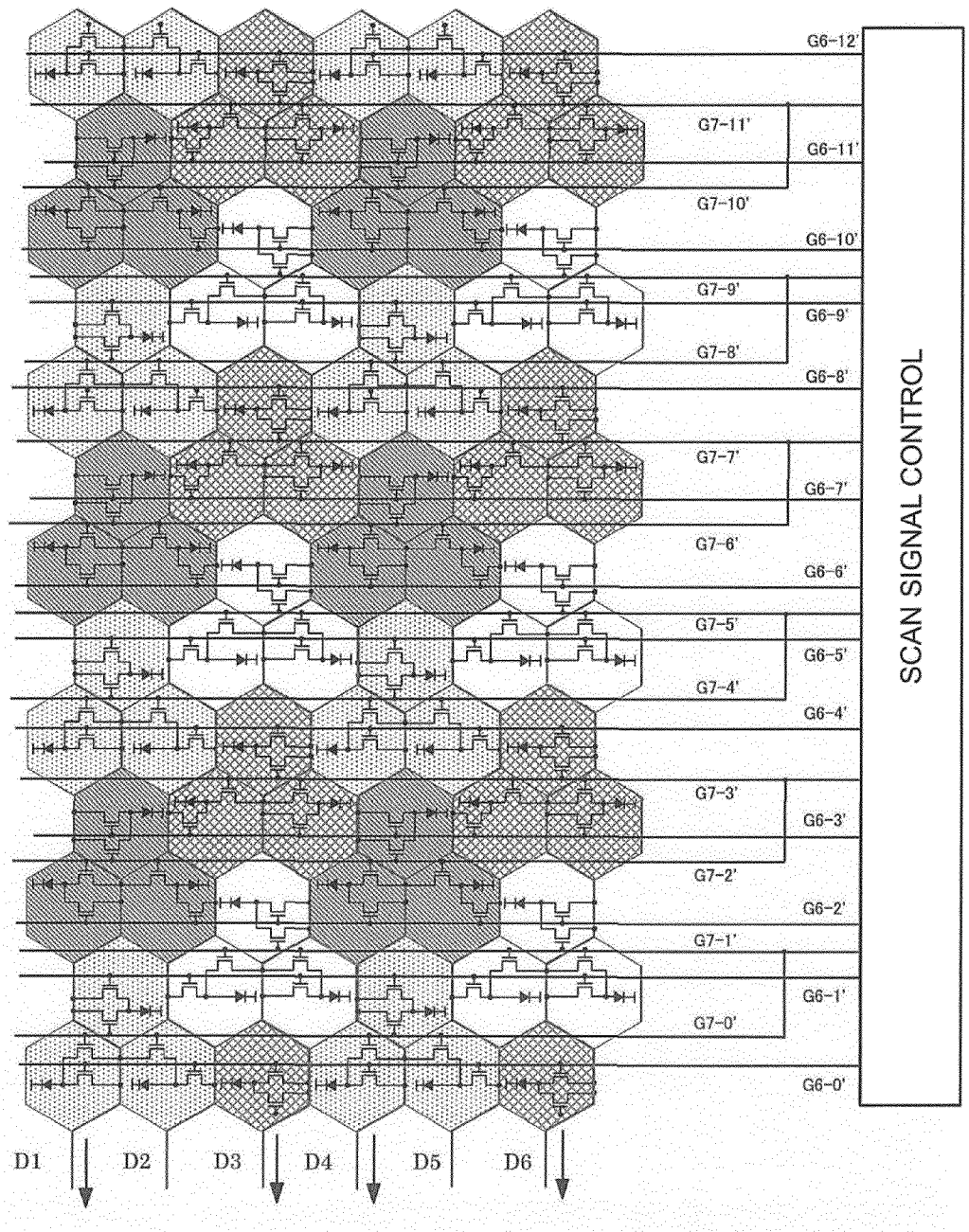
FIG. 13 is a drawing illustrating a simplified example of a radiation detector of the third exemplary embodiment applied to an indirect-conversion-type radiation detector.

FIG. 12 illustrates a simplified example of the radiation detector 42 of the first exemplary embodiment applied to an indirect-conversion-type radiation detector. FIG. 13 illustrates a simplified example of the radiation detector 342 of the third exemplary embodiment applied to an indirect-conversion-type radiation detector. Note that operations of the indirect conversion type radiation detectors illustrated in FIG. 12 and FIG. 13 are respectively similar to that of the radiation detector of the first exemplary embodiment and the radiation detector of the third exemplary embodiment, and therefore explanation thereof is omitted.

In each of the above exemplary embodiments, a case in which the common ground lines 30 are disposed on the insulating substrate 1, have been disclosed. However, there is no limitation thereto. For example, the common ground lines 30 may be disposed in any layer below the lower electrodes 11 as the pixel electrode that collect charges generated in the photoelectric conversion layer 6. In such case, the common ground lines 30 lowering the irradiation efficiency of radiation irradiated onto the sensor portions 103 may be prevented.

In the second exemplary embodiment and the fourth exemplary embodiment, cases in which the scan signal control sections (35a and 35b, or 435a and 435b) are respectively disposed along the column direction to the sides of the radiation detection element (110 and 410) of the radiation detector (142 and 442), have been described. However, the placements of the scan signal control sections (35a and 35b, or 435a and 435b) are not limited thereto. For example, in mammography applications, the scan signal control section (35a and 35b, or 435a and 435b) may be provided along the column direction at one side of the radiation detection element (110 and 410), with the other side along the column direction disposed on the side of the subject's chest wall. In such cases, two general purpose gate ICs may be employed as the scan signal control section (35a and 35b, or 435a and 435b) in a layered structure (double-layer) with scan lines G extending respectively therefrom, or scan lines G extending from a single custom gate IC.

[Fifth Exemplary Embodiment]

Specific explanation follows regarding an exemplary embodiment in which a radiation detector (42, 142, 342, 442) of each of the above exemplary embodiments is applied in mammography performed by tomosynthesis imaging.

Figure 14:
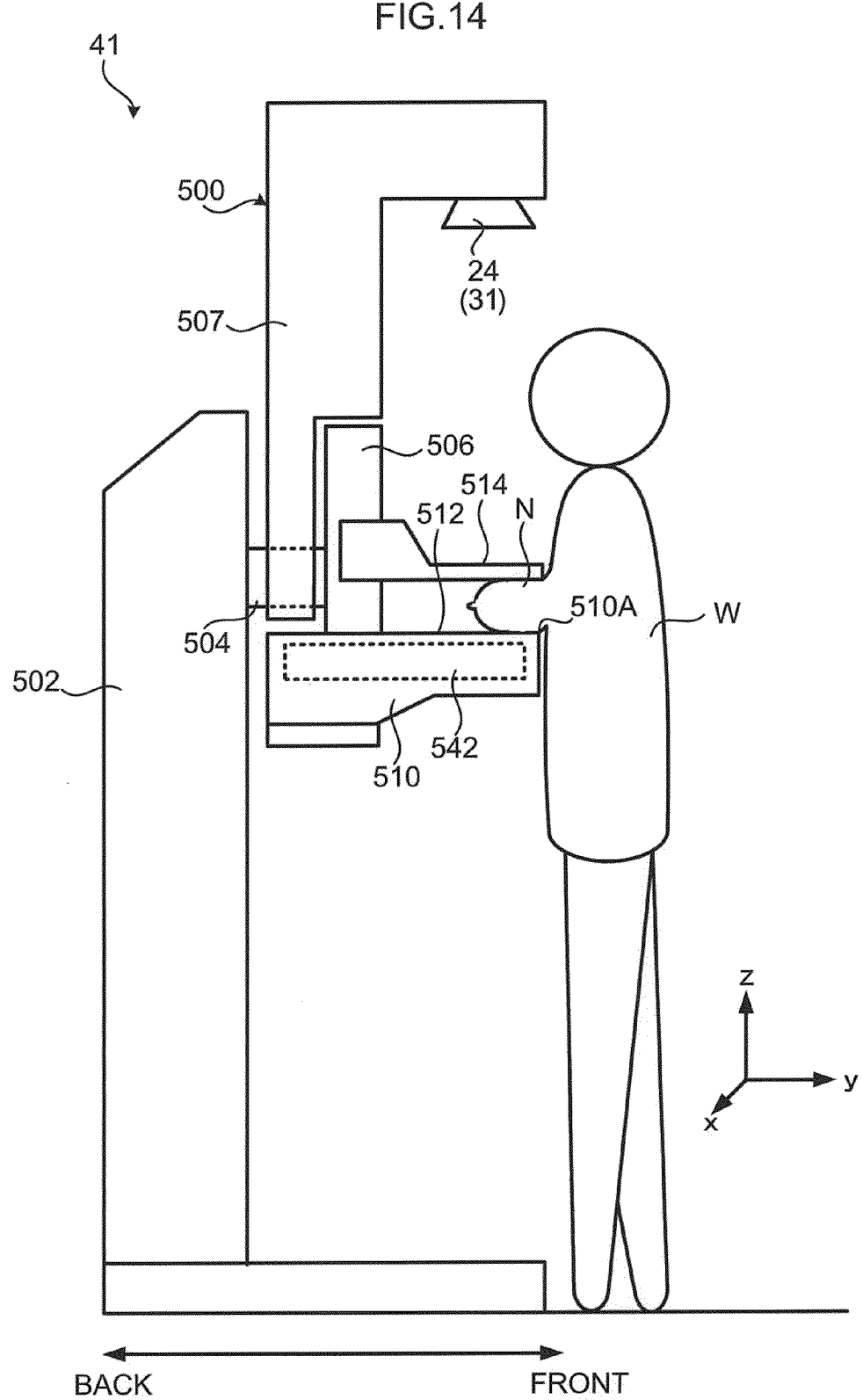
FIG. 14 is a schematic configuration diagram illustrating a configuration of an imaging apparatus for mammography of a fifth exemplary embodiment of the present invention.
Figure 15:
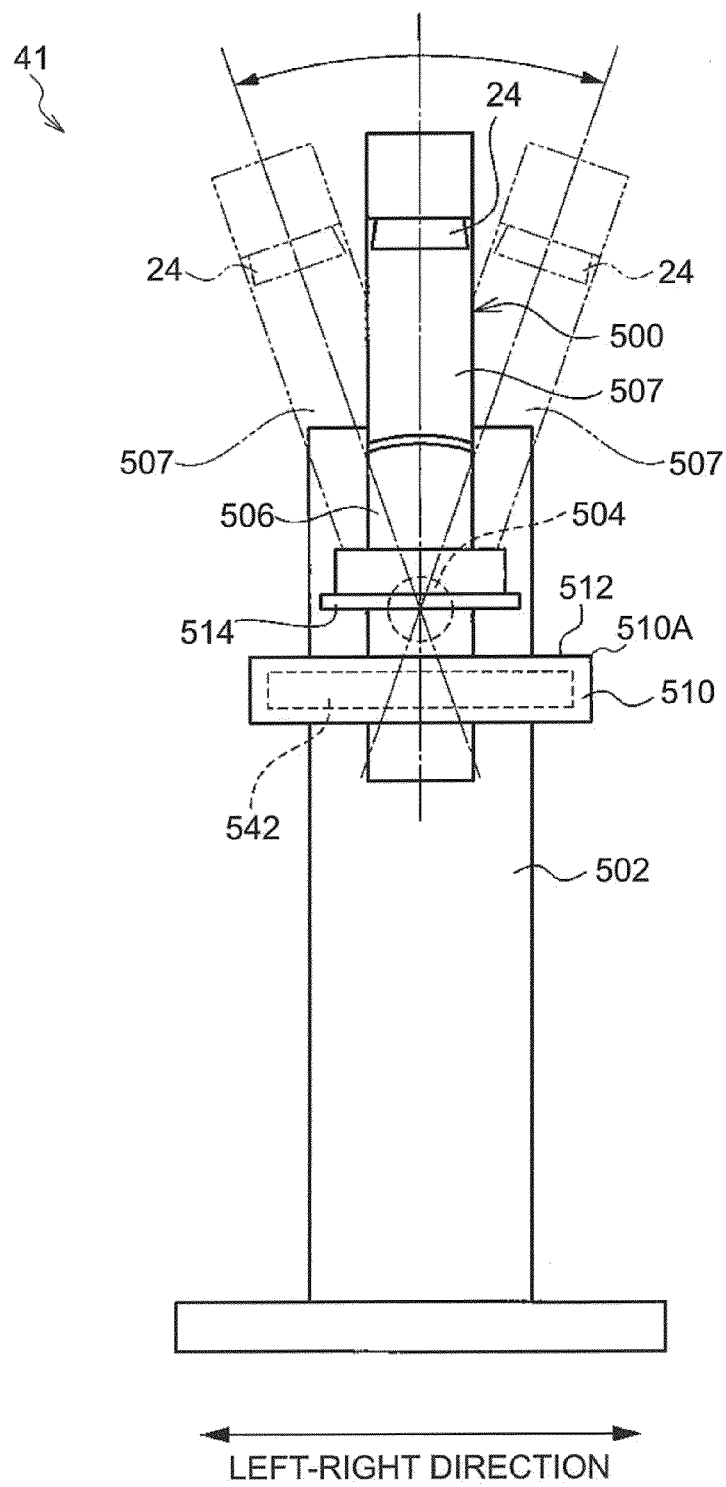
FIG. 15 is a configuration diagram illustrating a configuration of an imaging apparatus according to the fifth exemplary embodiment during imaging.
Figure 16:
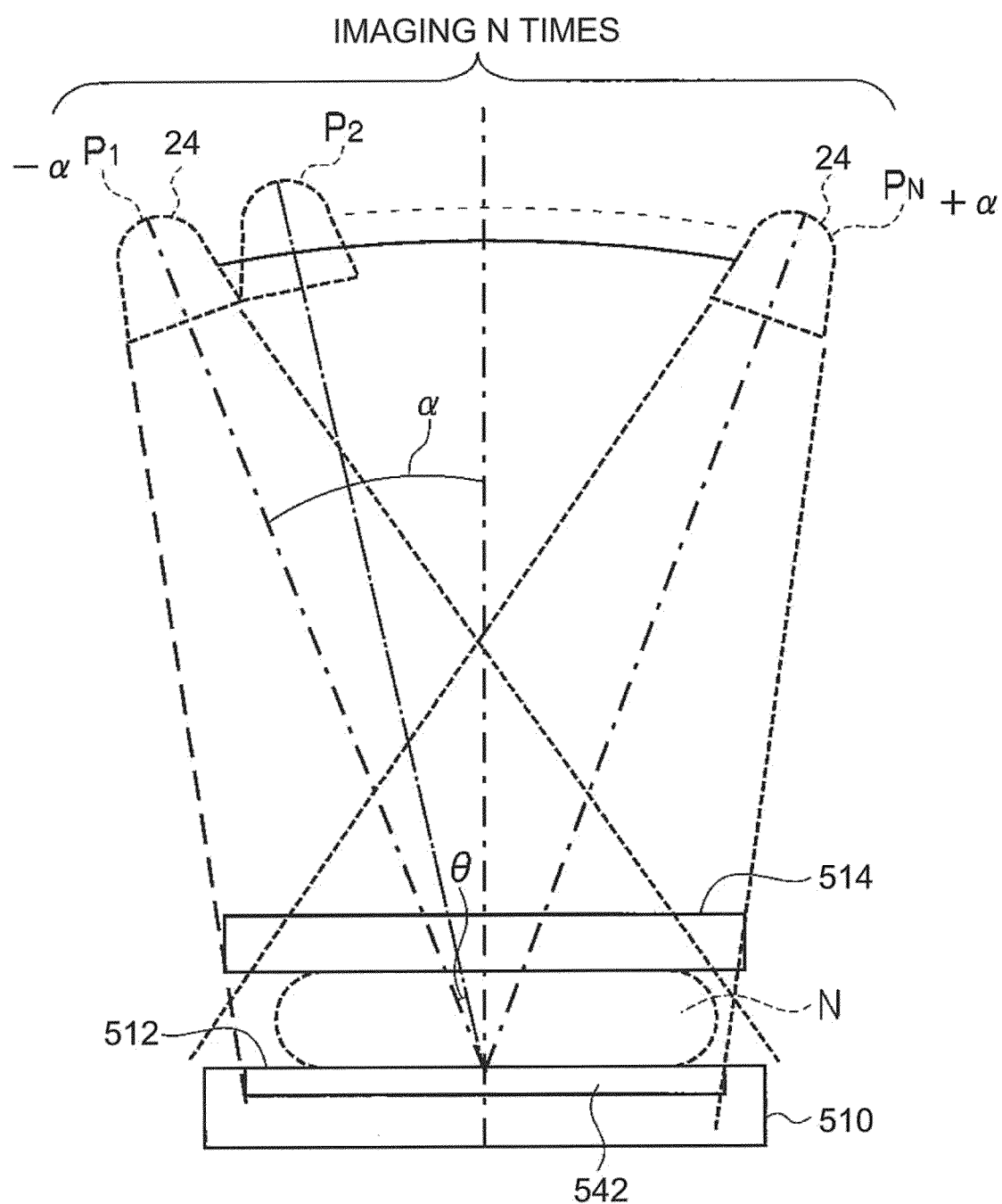
FIG. 16 is an explanatory diagram to explain an imaging apparatus according to the fifth exemplary embodiment during imaging.

FIG. 14 illustrates a schematic configuration of a configuration of an imaging apparatus 41 employed for mammography in the present exemplary embodiment. FIG. 15 is a configuration diagram of a configuration of the imaging apparatus 41 of the present exemplary embodiment during imaging. FIG. 16 is an explanatory diagram for explaining the imaging apparatus 41 of the present exemplary embodiment during imaging.

As illustrated in FIG. 14 to FIG. 16, the imaging apparatus 41 of the present exemplary embodiment is an apparatus that images a breast N of a subject W with radiation (for example X-rays) when the subject W is standing in an upright stance. Note that, in the following, the front side that is near to the subject W when the subject W is facing the imaging apparatus 41 during imaging is referred to as "the apparatus front side" of the imaging apparatus 41, and the far side that is positioned away from the subject W when the subject W is facing the imaging apparatus 41 is referred to as "the apparatus back side" of the imaging apparatus 41. Moreover, in the explanation, the left-right direction of the subject W when the subject W is facing the imaging apparatus 41 is referred to as "the apparatus left-right direction" of the imaging apparatus 41 (see each of the arrows in FIG. 14 to FIG. 16).

The imaging apparatus 41, as illustrated in FIG. 14, includes a measurement section 500 that is provided to the apparatus front side and is substantially C-shaped in side view, and a base stand section 502 that supports the measurement section 500 from the apparatus back side.

The measurement section 500 includes an imaging table 510 formed with a flat plane shaped imaging face 512 that makes contact with the breast N of the subject W who is in an upright stance, a pressing plate 514 for pressing the breast N between the pressing plate 514 and the imaging face 512 of the imaging table 510, and a holder section 506 that supports the imaging table 510 and the pressing plate 514.

The measurement section 500 is provided with a radiation source 31 such as a tube, a radiation irradiation section 24 that irradiates radiation for investigation from the radiation source 31 towards the imaging face 512, and a support section 507 that is separate from the holder section 506 and supports the radiation irradiation section 24.

A rotation shaft 504 supported by the base stand section 502 so as to be able to rotate is provided to the measurement section 500. The rotation shaft 504 is fixed to the support section 507 such that the rotation shaft 504 rotates as one with the support section 507.

The rotation shaft 504 is capable of switching between a state coupled to and rotating as one with the holder section 506, and a state in which the rotation shaft 504 is separate and rotates freely. Specifically, gears are respectively provided to the rotation shaft 504 and the holder section 506 with the gears configured capable of switching between a meshed state with each other and an unmeshed state. Note that switching between transmission and non-transmission of rotation force of the rotation shaft 504 can be accomplished using various mechanical elements.

The holder section 506 supports the imaging table 510 and the radiation irradiation section 24 such that the imaging face 512 and the radiation irradiation section 24 are separated from each other by a specific separation, and slidably retains the pressing plate 514 such that the separation between the pressing plate 514 and the imaging face 512 is variable. Note that the present exemplary embodiment is configured such that the position of the pressing plate 514 (the separation between the pressing plate 514 and the imaging face 512) is detectable. For example, a sensor (not shown in the drawings) may be provided to the sliding mechanism of the pressing plate 514, and the position of the pressing plate 514 detected by the sensor. Adopting such a configuration in the present exemplary embodiment enables the thickness of the breast N pressed by the pressing plate 514 to be detected.

The imaging face 512 that makes contact with the breast N is formed for example from a carbon composite from the perspectives of radiation transmissivity and strength. A radiation detector 542 is disposed inside the imaging table 510, and radiation irradiated through the breast N and the imaging face 512 is detected by the radiation detector 542. Note that the radiation detector 542 in the present exemplary embodiment may be any radiation detector (42, 142, 342, 442) of each of the above exemplary embodiments, and may be selected (changed) by a user according to the imaging.

The imaging apparatus 41 of the present exemplary embodiment is an apparatus capable of performing imaging from plural directions with respect to the breast N as the imaging subject. FIG. 15 and FIG. 16 respectively illustrate orientations of the imaging apparatus 41 during imaging, and positions of the radiation irradiation section 24 during imaging. As illustrated in FIG. 15 and FIG. 16, imaging is performed with the support section 507 tilted.

In the imaging apparatus 41, as illustrated in FIG. 16, when imaging (tomosynthesis imaging) is performed from plural directions with respect to the breast N, the rotation shaft 504 is free to rotate with respect to the holder section 506, and only the radiation irradiation section 24 moves in a circular arc shape due to the support section 507 rotating without the imaging table 510 or the pressing plate 514 moving. In tomosynthesis imaging, as illustrated in FIG. 16, the imaging position is moved from an angle α by a specific angle θ each time, and imaging is performed at N locations P1 to PN for the position of the radiation irradiation section 24.

In the present exemplary embodiment, as a specific example, a diagnosis mode and an imaging mode are provided as imaging modes, with these being selectable by a user such as a doctor. The diagnosis mode is a mode in which a user performs rough imaging of the imaging subject for such purposes as a diagnosis or diagnosis. As a specific example, in the present exemplary embodiment imaging is performed with a specific angle of 1 degree over a range of −10 degrees to +10 degrees. The imaging mode is a mode for performing imaging at higher definition than the imaging of the diagnosis mode. As a specific example, in the present exemplary embodiment imaging is performed with a specific angle of 1 degree over a range of −20 degrees to +20 degrees. Thereby in the present exemplary embodiment, when performing imaging to obtain a high definition image, imaging is performed by swinging over a large angle to increase the volume of data (image data volume).

Figure 17:
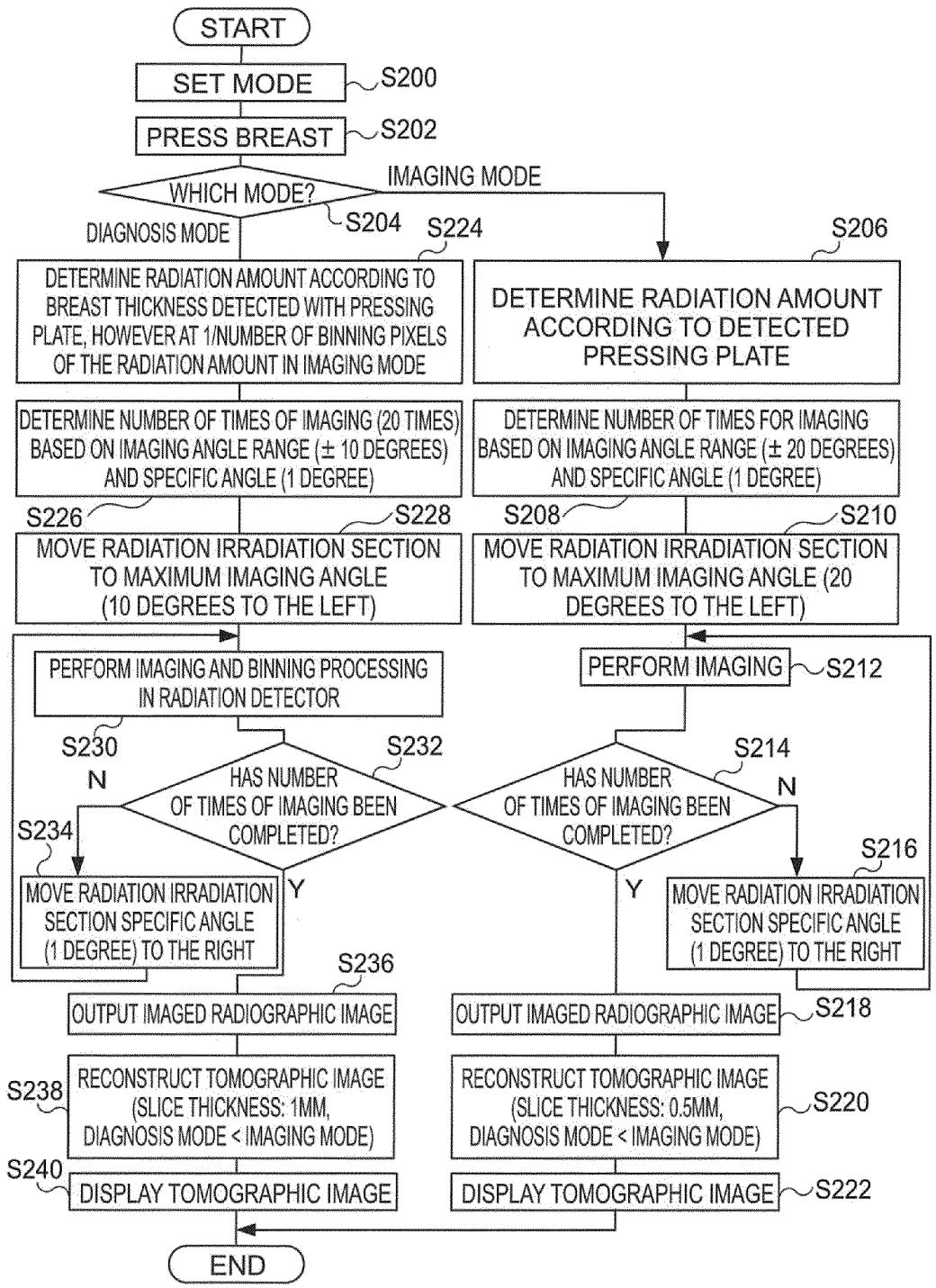
FIG. 17 is a flow chart illustrating a sequence of processing for imaging an image in a radiographic imaging system according to the fifth exemplary embodiment.

Explanation next follows regarding operation of the imaging apparatus 41 of the present exemplary embodiment. FIG. 17 is a flow chart illustrating a sequence of processing for imaging an image according to the present exemplary embodiment. When imaging is performed, imaging is executed according to an imaging menu in the imaging apparatus 41. When the imaging apparatus 41 is input with an imaging instruction to perform Cranial and Caudal (CC) imaging, the orientation of the holder section 506 is adjusted such that the imaging face 512 is in an upwards facing state, and the orientation of the support section 507 is adjusted such that the radiation irradiation section 24 is situated above the imaging face 512. When instruction is for Mediolateral-Oblique (MLO) imaging, the imaging table 510 is rotated a specific angle, and the orientation of the holder section 506 is adjusted to tilt the pressing plate 514.

At step S200 of FIG. 17, either the diagnosis mode or the imaging mode is set. There are no particular limitations to the setting method, and setting may be made based on an imaging menu when there is data indicating which mode contained in the imaging menu. Moreover setting may be made based on an instruction when a user instructs using for example an operation panel 44 and an operation input section 54.

A user contacts the breast N of the subject W with the imaging face 512 of the imaging apparatus 41. When in this state an operation instruction is given by a user to start pressing, at the next step S202, the imaging apparatus 41 moves the pressing plate 514 towards the imaging face 512, pressing the breast N.

When pressing of the breast N is complete, the user instructs imaging start using the operation panel 44 of the imaging apparatus 41 and the operation input section 54 of the image processing apparatus 50. The image processing apparatus 50 actuates the imaging apparatus 41 according to the instruction to start imaging, thereby imaging a radiographic image.

At the next step S204, determination is made as to whether the imaging mode is the diagnosis mode or the imaging mode. There are no particular limitations to the determination method, and determination may be made based on the setting of step S200.

Processing proceeds to step S206 when the mode is the imaging mode. At step S206 the radiation amount is determined according to the thickness of the breast N detected as described above. Due to the radiation amount reaching the radiation detector 42 (passing through the breast N) varying according to the thickness of the breast N, in the present exemplary embodiment, a correspondence relationship between the thickness of the breast N and the radiation amount irradiated is determined in advance. In step S206, the radiation amount irradiated is determined according to the thickness of the breast N based on the predetermined relationship.

At the next step S208, the number of times for imaging is determined based on the imaging angle range and the specific angle. As described above, in the present exemplary embodiment, as a specific example, in the imaging mode the imaging angle range is ±20 degrees and the specific angle is 1 degree in order to obtain a high definition image. The number of individual imaging times is accordingly determined as 40 times.

In the next step S210, the support section 507 is moved to the maximum imaging angle (20 degrees on the left in the present exemplary embodiment), and the radiation irradiation section 24 moved. Then, at the next step S212, radiation is irradiated from the radiation irradiation section 24 and the breast N is imaged. Note that, in this imaging, imaging is performed similarly to imaging with the normal processing of imaging processing of the first exemplary embodiment (see step S104 of FIG. 5). Namely, in order to read out charges from each of respective pixels 20, an ON signal is output in sequence one line at a time to scan lines (the first scan lines G1-0 to G1-7 in the first exemplary embodiment). The respective charge signals accumulated in a charge storage capacitor 5 of each of the pixels 20 is accordingly read, and a radiographic image is acquired by performing normal processing.

In the next step S214 determination is made as to whether or not imaging has been completed for the number of imaging times determined at step S208. Determination is negative and processing proceeds to step S216 when not complete. At step S216 the support section 507 is moved to the right by the specific angle=1 degree and the radiation irradiation section 24 is moved before the processing then returns to step S212 and the current processing repeated. However determination is affirmative and processing proceeds to step S218 when imaging has been completed for the determined number of times.

At step S218, the imaged radiographic images (40 times worth) are output from the radiation detector 42 to the image processing apparatus 50. Note that although in the present exemplary embodiment the total number of times worth of the radiographic images are output from the radiation detector 42 after imaging has been completed, there is no limitation thereto. Configuration may be made such that a radiographic image is output from the radiation detector 42 each time imaging is completed.

At the next step S220, the image processing apparatus 50 reconstructs a tomographic image based on the radiographic images obtained from the radiation detector 42. There are no particular limitations to the specification of the tomographic image reconstruction, and reconstruction of a tomographic image may be performed according to a known reconstruction method. Note that, in the present exemplary embodiment, the slice thickness (thickness of the tomographic image) during reconstruction of a tomographic image is predetermined according to the mode. In tomosynthesis imaging, generally the larger the angle of swing the higher the resolution in the depth direction, and the more detailed the data that can be obtained in the depth direction. In the present exemplary embodiment, more detailed depth direction data is obtained in the imaging mode due to imaging with a larger angle of swing in the imaging mode than in the diagnosis mode. Reconstruction is accordingly performed when imaging in the imaging mode with a thinner slice thickness than in the diagnosis mode. Note that, the slice thickness may be thinner in the imaging mode than in the diagnosis mode, and specific thicknesses in the present exemplary embodiment are 0.5 mm in the imaging mode and 1 mm in the diagnosis mode. However, there are no particular limitations thereto and, for example, the slice thickness may be determined according to the imaging angle. Moreover, there is no limitation to the above, and the slice thickness may be determined according to user instruction when slice thickness is user instructed.

In the next step S222, after instructing the reconstructed tomographic image to be displayed on a display 52 of the image processing apparatus 50 and on a display section 80A of a display device 80 the current processing is ended.

However, processing proceeds to step S224 when determination at step S204 is the diagnosis mode. At step S224, the radiation amount is determined according to the thickness of the breast N, similarly to as in step S206 of the imaging mode. However, in the diagnosis mode, the radiation amount for irradiation each time of imaging is made smaller, according to the content of binning processing, than in the imaging mode in which binning processing is not performed. For example, when binning processing is performed with 4 pixels 20 as a pixel group, as in the first exemplary embodiment and the second exemplary embodiment, where each pixel group is treated as a single pixel, the radiation amount is ¼ the radiation amount when imaging by performing normal processing such that the radiation amount per single pixel is the same as when normal processing is performed. Moreover, when binning processing is performed with 3 pixels 20 as a pixel group, as in the third exemplary embodiment and the fourth exemplary embodiment, where each pixel group is treated as a single pixel, the radiation amount is ⅓ the radiation amount when imaging by performing normal processing such that the radiation amount per single pixel is the same as when normal processing is performed.

In the next step S226, similarly to in step S208 of the imaging mode, the number of times of imaging is determined based on the imaging angle range and the specific angle. As a specific example in the present exemplary embodiment, as explained above, in the diagnosis mode, the imaging angle range is ±10 degrees and the specific angle is 1 degree in order to perform rough imaging. The number of individual times for imaging is accordingly determined as 20 times.

In the next step S228, similarly to step S210 in the imaging mode, the support section 507 is moved to the maximum imaging angle (10 degrees on the left in the present exemplary embodiment), and the radiation irradiation section 24 moved. Then at the next step S230, radiation is irradiated from the radiation irradiation section 24 and the breast N is imaged, and the radiation detector 42 also performs binning processing. Note that imaging and binning processing is performed here similarly (step S106 of FIG. 5). Namely, in order to read out charges from each of the respective pixel groups, an ON signal is output to scan lines (for example to the second scan lines G2 and the third scan lines G3 in the first exemplary embodiment) and binning processing is performed treating each of the pixel groups as a single pixel. The respective charge signals of each of the pixels viewed as a signal pixel is accordingly read and binning processing performed thereon. A binning-processed radiographic image is accordingly acquired in the radiation detector 42.

In the next step S232, similarly to in step S214 in the imaging mode, determination is made as to whether or not imaging has been completed for the number of imaging times determined at step S226. Determination is negative and processing proceeds to step S234 when not complete. At step S234 the support section 507 is moved to the right by the specific angle=1 degree and the radiation irradiation section 24 is moved before the processing then returns to step S230, and the current processing repeated. However determination is affirmative and processing proceeds to step S236 when imaging has been completed for the determined number of times. At step S236, similarly to in step S218 in the imaging mode, the imaged radiographic images (20 times worth) are output from the radiation detector 42 to the image processing apparatus 50.

At the next step S238, the image processing apparatus 50 reconstructs a tomographic image based on the radiographic images obtained from the radiation detector 42. Similarly to in step S220 in the imaging mode, there are no particular limitations to the specification of the tomographic image reconstruction, and reconstruction of a tomographic image may be performed according to a known reconstruction method. Note that as stated above, in the present exemplary embodiment, the slice thickness (thickness of tomographic image) when reconstructing the tomographic images is 1 mm in the diagnosis mode, this being thicker than in the imaging mode.

In the next step S240, after instructing the reconstructed tomographic image to be displayed on the display 52 of the image processing apparatus 50 and on the display section 80A of the display device 80 the current processing is ended.

When performing tomosynthesis imaging as in the present exemplary embodiment, high speed imaging may be performed due to having a smaller imaging angle range and a smaller number of times of imaging in the diagnosis mode for performing rough imaging. Binning processing may also be performed. Moreover, due to having a smaller radiation amount for irradiation when performing binning processing, more specifically due to controlling the radiation amount per pixel group (treated as one pixel) to be the same amount as the radiation amount per pixel in the imaging mode, then radiation dose to the subject W may be reduced. Moreover, in the imaging mode, a larger amount of data (image data) may be obtained due to the imaging angle range being larger (swinging over a large imaging angle). In particular, detailed data may be obtained in the depth direction. Accordingly a high definition image may be obtained.

Note that although in the present exemplary embodiment explanation has been given of a specific example with the imaging apparatus 41 performing tomosynthesis imaging and applied to mammography, there is no limitation thereto. It should be noted that the processing for imaging images and the image display processing of the present exemplary embodiment may be similarly applied to the imaging apparatus 41 performing tomosynthesis imaging to other sites.

Moreover, in the present exemplary embodiment, although explanation has been given of a case in which instructions related to imaging are given by a user employing the operation panel 44 of the imaging apparatus 41 and the operation input section 54 of the image processing apparatus 50, there is no limitation thereto. For example, configuration wherein a user performs instruction employing a separately provided device such as a console.

In addition, the configurations, operations and the like of the radiation imaging system, the radiation detector, the pixels and the like that were described in the present exemplary embodiment are examples, and may, of course, be changed in accordance with the situation within a range that does not deviate from the gist of the present invention.

Further, in the present exemplary embodiment, the radiation of the present invention is not particularly limited, and X-rays, γ-rays or the like can be used.

What is claimed is:

1. A radiographic image detector comprising:
    a detection section including a plurality of pixels having hexagonal shaped pixel regions arrayed in a honeycomb pattern, each pixel including,
        a sensor portion that generates charges according to irradiated radiation,
        a first switching element that reads out the generated charges, and
        a second switching element that reads out the generated charges;
    a plurality of first scan lines, disposed one for each of a plurality of pixel rows configured by a plurality of the pixels adjacent to each other along a row direction, that are connected to a control terminal of the first switching element in each of the pixels of the corresponding pixel row;
    a plurality of second scan lines, disposed one for each of the plurality of pixel rows, that are split into a plurality of line-groups and are connected to control terminals of the second switching elements of the pixel groups belonging to each respective group such that, when combining and reading charges from a plurality of pixel groups each configured from a plurality of adjacent pixels in the plurality of pixel rows, charge signals corresponding to combined charge amounts read out from the respective plurality of pixel groups are transmitted through different respective data lines; and
    a plurality of data lines, disposed so as to respectively intersect with the plurality of first scan lines and the plurality of second scan lines, that transmit first charge signals corresponding to charges read out by the first switching elements in each of the plurality of pixels, and that transmit second charge signals corresponding to the combined charge amounts read by the second switching elements of the respective plurality of pixel groups,
    wherein combinations of the pixels configuring respective pixel groups are determined such that, when a plurality of hexagonal shaped regions are formed adjacent to each other, the plurality of hexagonal shape regions results in a honeycomb pattern array, and wherein each of the hexagonal shape regions are formed by including inside one center of gravity of a region surrounded by an outline of the plurality of pixel groups configured by the respective 3 pixels or the respective 4 pixels, and by connecting together 6 individual centers of gravity present at the periphery of the one center of gravity.

2. The radiographic image detector of claim 1, wherein, when each of the plurality of pixel groups is configured from 3 pixels, control terminals of the second switching elements of each of the pixels in respective of the plurality of pixel groups alongside each other in a row direction are respectively connected to the second scan lines, and adjacent scan lines are commonly connected as a single line-group.

3. The radiographic image detector of claim 2, wherein the 3 pixels are 3 pixels disposed such that two adjoining sides of each of the pixels are respectively adjacent to one side of each of the other two pixels.

4. The radiographic image detector of claim 1, wherein, when the plurality of pixel groups are each configured by 4 pixels, the second scan lines are commonly connected in a line-group configured by an adjacent pair of the second scan lines, each pair of the second scan lines being configured by a second scan line connected to control terminals of the second switching elements of 3 individual pixels in a plurality of respective pixel groups alongside each other in the row direction, and the second scan line connected to the control terminals of the second switching elements of one individual pixel in each of the plurality of pixel groups.

5. The radiographic image detector of claim 4, wherein the 4 pixels are configured by 4 pixels made up from 3 pixels disposed such that two adjoining sides of each of the pixels are respectively adjacent to one side of the other 2 pixels out of the 3 pixels, and by 1 pixel disposed such that two adjoining sides are respectively adjacent to one side of 2 pixels out of the 3 pixels.

6. The radiographic image detector of claim 1, wherein the second switching elements connected to the plurality of second scan lines are controlled as blocks with shifted timings for each of the line-groups.

7. The radiographic image detector of claim 1, wherein the hexagonal shaped pixel regions are formed as regular hexagonal shapes.

8. The radiographic image detector of claim 1, wherein the hexagonal shaped pixel regions are formed as flattened hexagonal shapes.

9. The radiographic image detector of claim 8, wherein the hexagonal shaped pixel regions are formed flattened such that one diagonal line out of 3 diagonal lines passing through the center of each of the pixel regions is shorter than the other two diagonal lines and the other two diagonal lines are of equal length to each other.

10. The radiographic image detector of claim 1, wherein the plurality of data lines are laid out bent along one portion of the hexagonal shaped pixel region periphery.

11. The radiographic image detector of claim 1, wherein the sensor portions includes a semiconductor film that receives irradiation with the radiation and generates charges, and
    wherein, the charges are accumulated in a storage capacitor provided in each of the plurality of pixels and the charges accumulated in the storage capacitor are read by the first switching element and the second switching element.

12. The radiographic image detector of claim 11 further comprising, a plurality of common lines that connect together one electrode of each of the storage capacitors and that fixes the electrodes to a specific electrical potential.

13. The radiographic image detector of claim 12, wherein the plurality of common lines extend between the plurality of data lines in a straight line shape or in a substantially straight line shape.

14. The radiographic image detector of claim 13, wherein the plurality of common lines are connected to the plurality of data lines through the storage capacitors, the first switching elements and the second switching elements.

15. The radiographic image detector of claim 14, wherein the plurality of first scan lines, the plurality of second scan lines, the plurality of data lines, the plurality of common lines, the first switching elements, and the second switching elements, are disposed at a lower layer side of the sensor portions.

16. The radiographic image detector of claim 1, wherein the sensor portions includes a scintillator that converts the radiation that has been irradiated into visible light, and wherein, after the converted visible light has been converted into charges by a semiconductor layer, the charges are read out by the first switching element and the second switching element.

17. A radiographic imaging apparatus comprising:
the radiographic image detector of claim 1; and
a radiation irradiation section provided facing the radiographic image detector and that irradiates radiation onto an imaging subject above the radiographic image detector,
wherein a radiographic image is imaged with the radiographic image detector.

18. The radiographic imaging apparatus of claim 17, wherein the radiation irradiation section irradiates radiation onto the imaging subject from each of a plurality of different imaging angles.

19. A radiographic imaging system comprising:
the radiographic imaging apparatus of claim 18;
control section that instructs the radiographic imaging apparatus to perform imaging of a radiographic image, and that acquires a plurality of radiographic images from the radiographic image detector that have been imaged by the radiographic image detector at each of the imaging angles; and
tomographic image generation section that generates a plurality of tomographic images reconstructed with reference to a detection face of the radiographic image detector based on the plurality of radiographic images acquired by the control section;
wherein the control section includes, switching section that, based on an external instruction, switches between a first radiographic image acquisition mode that acquires a first radiographic image configured from image data in single-pixel units of a radiographic image detection device, and a second radiographic image acquisition mode that acquires a second radiographic image configured from image data in multi-pixel units of the radiographic image detection device, and
wherein the radiation irradiation section has a range of image angles for irradiating radiation onto the imaging subject that is larger when imaging to acquire the first radiographic image than when imaging to acquire the second radiographic image.

20. The radiographic imaging system of claim 19, wherein the thickness of the tomographic image generated by the tomographic image generation section based on the first radiographic images is thinner than the thickness of the tomographic images generated based on the second radiographic images.

21. A radiographic imaging system comprising:
the radiographic imaging apparatus of claim 17; and
control section that instructs the radiographic imaging apparatus to perform imaging of a radiographic image, and that acquires a radiographic image from the radiographic imaging apparatus,
wherein the control section includes, switching section that, based on an external instruction, switches between a first radiographic image acquisition mode that acquires a first radiographic image configured from image data in single-pixel units of a radiographic image detection device, and a second radiographic image acquisition mode that acquires a second radiographic image configured from image data in multi-pixel units of the radiographic image detection device.

22. The radiographic imaging system of claim 21, wherein, when instructed to perform imaging to acquire the second radiographic image, the control section controls the radiation irradiation section such that the radiation amount irradiated onto the imaging subject is an amount according to the multi-pixel unit and smaller than when imaging to acquire the first radiographic image.

* * * * *